US009474222B2

(12) United States Patent
Van Heusden et al.

(10) Patent No.: US 9,474,222 B2
(45) Date of Patent: Oct. 25, 2016

(54) PARTHENOCARPY GENES IN TOMATO

(75) Inventors: Adriaan Willem Van Heusden, Wageningen (NL); Benoit Gorguet, Nijmegen (NL)

(73) Assignee: Monsanto Invest B.V., Bergschenhoek (NL)

( * ) Notice: Subject to any disclaimer, the term of this patent is extended or adjusted under 35 U.S.C. 154(b) by 1183 days.

(21) Appl. No.: 12/667,672

(22) PCT Filed: Jun. 4, 2008

(86) PCT No.: PCT/NL2008/050348
§ 371 (c)(1),
(2), (4) Date: Jan. 28, 2010

(87) PCT Pub. No.: WO2009/005343
PCT Pub. Date: Jan. 8, 2009

(65) Prior Publication Data
US 2011/0016549 A1   Jan. 20, 2011

Related U.S. Application Data

(60) Provisional application No. 60/948,029, filed on Jul. 5, 2007.

(30) Foreign Application Priority Data

Jul. 5, 2007   (EP) ..................... 07111791
Oct. 22, 2007  (EP) ..................... 07119009

(51) Int. Cl.
*A01H 5/10*   (2006.01)
*A01H 1/02*   (2006.01)
*A01H 5/08*   (2006.01)

(52) U.S. Cl.
CPC  *A01H 5/10* (2013.01); *A01H 1/02* (2013.01); *A01H 5/08* (2013.01)

(58) Field of Classification Search
CPC ............. A01H 1/04; A01H 5/08; A01H 1/02
USPC ................................ 800/267, 317.4
See application file for complete search history.

(56) References Cited

U.S. PATENT DOCUMENTS

2010/0146656 A1   6/2010  de Haan et al.

FOREIGN PATENT DOCUMENTS

| EP | 1428425 | 6/2004 |
|---|---|---|
| EP | 1 057 401 | 12/2010 |
| WO | WO 98/24301 | 6/1998 |
| WO | WO 99/21411 | 5/1999 |
| WO | WO 2000/074468 | 12/2000 |
| WO | WO 2006/046861 | 5/2006 |

OTHER PUBLICATIONS

Gorguet et al (Plant Biol 7: 131-139, 2005, cited in the IDS filed Nov. 11, 2010).*
Baggett et al (HortScience 32(7): 1299-1300, 1997).*
Beraldi et al (Theor Appl Genet 108: 209-216, 2004).*
Chetelat et al (Theor Appl Genet 100: 232-241, 2000).*
Finkers et al (Theor Appl Genet 114: 1071-1080, 2007 (published online Feb. 2, 2007)), cited on the Nov. 11, 2010 IDS.*
Zijlstra (Zaadbelangen 4: 92-94, 1985), cited on the Nov. 11, 2010 IDS.*
Zijlstra, Parthenocarpie in tomaat: twee nieuwe lijen uit sortkruising, Zaadbelangen, 4:92-94 (1985).
Finkers, The Genetics of Botrytis Cinerea Resistance in Tomato, PhD Thesis Wageningen University, 1-120, 2007.
Finkers, The Construction of a Solanum Habrochaites LYC4 Introgression Line Population and the Identification . . . , Theor Appl Genet, 114, 1071-1080 , 2007.
Zijlstra, Parthenocarpie in Tomaat: Twee Nieuwe Lijnen Uit Soortkruising, Zaadbelangen, 4, 92-94, 1985.
Brouwer, Fine Mapping of Three Quantitative Trait Loci for Late Blight Resistance . . . , Theor Appl Genet, 108, 628-638, 2004.
Coaker, Mapping, Genetic Effects, and Epistatic Interaction . . . , Theor Appl Genet, 108, 1047-1055, 2004.
Gorguet, Pathenocarpic Fruit Development in Tomato, Plant Biol., 7, 131-139, 2005.
Baggett et al., "Siletz' Parthenocarpic Tomato," Hort. Science 32(7):1299-1300, 1997.
Bai et al., "QTLs for Tomato Powdery Mildew Resistance (*Oidium lycopersici*) in *Lycopersicon parviflorum* G1.1601 Co-localize with Two Qualitative Powdery Mildew Resistance Genes," *MPMI* 16(2):169-176, 2003.
Bernacchi et al., "Advanced backcross TL analysis in tomato. I. Identification of TLs for traits of agronomic importance from *Lycopersicon hirsutum*," *Theor. Appl. Genet.* 97:381-397, 1998.
Department of Horticulture, Purdue University, "Tomato Genetics Cooperative Report," 36:1 and 68, 1986.
Gorguet et al., "Mapping and characterization of novel parthenocarpy QTLs in tomato," *Theor. Appl. Genet.* 116:755-767, 2008.
Haanstra et al., "An integrated high-density RFLP-AFLP map of tomato based two *Lycopersicon esculentum* x *L. pennellii* $F_2$ populations," *Theor. Appl. Genet.* 99:254-271, 1999.
International Search Report regarding International Application No. PCT/NL2008/050296, dated Oct. 2, 2008.
Mazzucato et al., "The parthenocarpic fruit (pat) mutant of tomato (*Lycopersicon esculentum* Mill.) sets seedless fruits and has aberrant anther and ovule development," *Development* 125:107-114, 1998.

* cited by examiner

*Primary Examiner* — Keith Robinson
(74) *Attorney, Agent, or Firm* — Dentons US LLP

(57) ABSTRACT

The present invention relates to *Solanum lycopersicum* plants carrying one or more of the pat-6, pat-7, pat-8 and pat-9 parthenocarpy genes. Preferred plants comprise a pair of pat-6 and pat-7 genes or a pair of pat-8 and pat-9 genes, whereby preferably the plant is homozygous for at least one of the two genes in the pair, more preferably the plant is homozygous for both genes in the pair. Such plants are capable of producing seedless tomatoes. The invention further relates to methods for producing plants carrying one or more of the pat-6, pat-7, pat-8 and pat-9 parthenocarpy genes using marker-assisted breeding.

24 Claims, 5 Drawing Sheets

PARTHENOCARPY GENES IN TOMATO

RELATED APPLICATIONS

The present application is a U.S. National Phase Application of International Application No. PCT/NL2008/050348 (filed Jun. 4, 2008), which claims priority to U.S. Provisional Patent Application No. 60/948,029 (filed Jul. 5, 2007), and to European Patent Application Nos. 07111791.5 (filed Jul. 5, 2007) and 07119009.4 (filed Oct. 22, 2007), all of which are hereby incorporated by reference in their entirety.

SEQUENCE LISTING SUBMISSION VIA EFS-WEB

A computer readable text file, entitled "067131-5019-SeqListing.txt," created on or about Jan. 4, 2010, with a file size of about 5 kb contains the sequence listing for this application and is hereby incorporated by reference in its entirety.

FIELD OF THE INVENTION

The present invention relates to *Solanum lycopersicum* plants carrying parthenocarpy genes the presence of which may be assessed by their genetic linkage to molecular markers. The invention further relates to seed of the plants and to seedless tomatoes obtainable from the plants, as well as to methods for obtaining the plants using the molecular markers linked to parthenocarpy genes for assistence in breeding.

BACKGROUND OF THE INVENTION

In normal fruit development, the initiation of fruit set depends on the successful completion of pollination and fertilization. However, these processes depend on narrow environmental constrains (Picken 1984). Good pollen production is permitted by night a temperature ranging between 15 and 21° C., and air circulation is necessary to ensure pollen shedding. In tomato, failure to fruit set is therefore a common phenomenon under certain field conditions (high or low humidity combined with low or high temperatures) and in unheated greenhouses or tunnels during winter or early spring cultivation (George et al. 1984). Parthenocarpic fruit development, which is the growth of the ovary into a seedless fruit in absence of pollination and/or fertilization, offers an opportunity to overcome this problem of poor fruit set under harsh conditions. In tomato three sources of natural parthenocarpy have been widely studied because of their perspectives for practical application to produce seedless fruits (reviewed by Gorguet et al. 2005): Soressi or Montfavet 191 (pat), Severianin (pat-2) and RP75/59 (pat-3/pat-4). In addition, two other sources of parthenocarpy in tomato, IVT-line 1 and 2 (Zijlstra 1985), were found to give a higher and more stable level of parthenocarpy than Soressi and Severianin, though no detailed study has ever been performed on them. Parthenocarpy in IVT-line 1 originated from *S. habrochaites* and was thought to be monogenic. Parthenocarpy in IVT-line 2 originated from *S. peruvianum* and was assumed to be polygenic. To date, the only mapped gene for parthenocarpy in tomato is pat-1, which is localized on the long arm of Chromosome 3 (Beraldi et al. 2004).

It is therefore an object of the present invention to provide for novel genes for parthenocarpic fruit.

DESCRIPTION OF THE INVENTION

Definitions

In this description, unless indicated otherwise, the terms and definitions used herein are those used in (Mendelian) genetics, for which reference is made to M. W. Strickberger, Genetics, second Edition (1976), in particular pages 113-122 and 164-177. As mentioned therein, "gene" generally means an inherited factor that determines a biological characteristic of an organism (i.e. a tomato plant), an "allele" is an individual gene in the gene pair present in the (diploid) tomato plant. In this context it is understood that the term pat- or se-gene as used herein refer to a pat- or se-allele of the respective genes that is capable of producing or contributing to the parthenocarpic or functionally sterile phenotypes of the invention, respectively.

A plant is called "homozygous" for a gene when it contains the same alleles of said gene, and "heterozygous" for a gene when it contains two different alleles of said gene. The use of capital letters indicates a dominant (form of a) gene and the use of small letters denotes a recessive gene: "X,X" therefore denotes a homozygote dominant genotype for gene or property X; "X,x" and "x,X" denote heterozygote genotypes; and "x,x" denotes a homozygote recessive genotype. As commonly known, only the homozygote recessive genotype will generally provide the corresponding recessive phenotype (i.e. lead to a plant that shows the property or trait "x") whereas the heterozygotic and homozygote dominant genotypes will generally provide the corresponding dominant phenotype (i.e. lead to a plant that shows the property or trait "X"), unless other genes and/or factors such as multiple alleles, suppressors, codominance etc. (also) play a role in determining the phenotype.

As a general rule, hybrid seed is obtained by crossing two different parent tomato plants, which most often belong to different lines. Using cultivation techniques and plant breeding techniques known per se, such hybrids can be provided with highly specific, desired properties, which makes it possible to "design" the hybrids, i.e. to confer to the hybrid plants predetermined inheritable characteristics. This is usually achieved by suitably choosing (the properties of) the two parent lines which are crossed to provide the hybrid seed. These are usually inbred lines, obtained by self-fertilization (self-pollination) over several generations, and such inbred lines will usually again have been specifically "designed" by the breeder so as to provide hybrid offspring with the desired properties, when crossed with another—usually predetermined—inbred parent line. As a rule, such parent lines will be genetically homozygote and identical (i.e. as a result of inbreeding) so that they can provide, in a stable and reliable manner, genetically uniform—albeit heterozygote—hybrid line combinations, which can combine the properties of the parent lines. In doing so, the aim is on the one hand to cross certain properties from the parent lines as purely as possible into the seed, while on the other hand use is made of the known effect of heterosis or inbred growth, which can provide improved properties regarding—inter alia—the growth of plants and fruits and thereby of the yield. This heterosis effect is obtained when/because the parent lines used are not related with respect to certain genetic properties (i.e. when the parent lines genetically "lie far apart"). For a further description of plant breeding techniques in general, and tomatoes in particular, using classical cultivation techniques, including the formation of hybrids, reference is made to the known handbooks, the contents of which are incorporated herein by reference.

As used herein, the term "plant" includes the whole plant or any parts or derivatives thereof, such as plant cells, plant protoplasts, plant cell tissue cultures from which tomato plants can be regenerated, plant calli, plant cell clumps, and plant cells that are intact in plants, or parts of plants, such as embryos, pollen, ovules, fruit (e.g. harvested tomatoes), flowers, leaves, seeds, roots, root tips and the like.

Botanical terminology: Linnaeus is considered the father of botanical classification. Although he first categorized the modern tomato as a *Solanum*, its scientific name for many years has been *Lycopersicon esculentum*. Similarly, the wild relatives of the modern tomato have been classified within the *Lycopersicon* genus, like *L. pennellii*, *L. hirsutum*, *L. peruvianum*, *L. chilense*, *L. parviflorum*, *L. chmielewskii*, *L. cheesmanii*, *L. cerasiforme*, and *L. pimpinellifolium*. Over the past few years, there has been debate among tomato researchers and botanists whether to reclassify the names of these species. The newly proposed scientific name for the modern tomato is *Solanum lycopersicum*. Similarly, the names of the wild species may be altered. *L. pennellii* may become *Solanum pennellii*, *L. hirsutum* may become *S. habrochaites*, *L. peruvianum* may be split into *S. 'N peruvianumr'* and *S. 'Callejon de Huayles'*, *S. peruvianum*, and *S. corneliomuelleri*, *L. parviflorum* may become *S. neorickii*, *L. chmeilewskii* may become *S. chmielewskii*, *L. chilense* may become *S. chilense*, *L. cheesmaniae* may become *S. cheesmaniae* or *S. galapagense*, and *L. pimpinellifolium* may become *S. pimpinellifolium* (Solanacea Genome Network (2005) Spooner and Knapp; www.sgn.cornell.edu/help/about/*solanum*_nomenclature.html).

Nucleic acid sequences or fragments comprising pat or se genes and alleles may also be defined by their capability to "hybridise" with any of the *S. habrochaites* pat or se genes and alleles as herein defined, under moderate, or preferably under stringent hybridisation conditions. Stringent hybridisation conditions are herein defined as conditions that allow a nucleic acid sequence of at least about 25, preferably about 50 nucleotides, 75 or 100 and most preferably of about 200 or more nucleotides, to hybridise at a temperature of about 65° C. in a solution comprising about 1 M salt, preferably 6×SSC or any other solution having a comparable ionic strength, and washing at 65° C. in a solution comprising about 0.1 M salt, or less, preferably 0.2×SSC or any other solution having a comparable ionic strength. Preferably, the hybridisation is performed overnight, i.e. at least for 10 hours and preferably washing is performed for at least one hour with at least two changes of the washing solution. These conditions will usually allow the specific hybridisation of sequences having about 90% or more sequence identity. Moderate conditions are herein defined as conditions that allow a nucleic acid sequences of at least 50 nucleotides, preferably of about 200 or more nucleotides, to hybridise at a temperature of about 45° C. in a solution comprising about 1 M salt, preferably 6×SSC or any other solution having a comparable ionic strength, and washing at room temperature in a solution comprising about 1 M salt, preferably 6×SSC or any other solution having a comparable ionic strength. Preferably, the hybridisation is performed overnight, i.e. at least for 10 hours, and preferably washing is performed for at least one hour with at least two changes of the washing solution. These conditions will usually allow the specific hybridisation of sequences having up to 50% sequence identity. The person skilled in the art will be able to modify these hybridisation conditions in order to specifically identify sequences varying in identity between 50% and 90%.

DETAILED DESCRIPTION OF THE INVENTION

Finkers et al. (2007b) have recently developed a set of introgression lines for *S. habrochaites* accession LYC4 in the *S. lycopersicum* cv. Moneymaker genetic background. Parthenocarpic fruit development and style exertion was observed in one of the introgression lines (IL5-1), which carries the short arm of Chromosome 4 of *S. habrochaites* in homozygous state and the complete Chromosome 5 of *S. habrochaites* in homozygous or heterozygous state (unpublished personal communication).

The present inventors have now characterized and mapped two novel parthenocarpy genes (one major and one minor) that are responsible for the seedless fruit development in IL5-1. In addition the position of the style exertion locus was also identified. Furthermore two further parthenocarpy genes combined from IVT-line 1 were identified and mapped, using an $F_2$ segregating population.

In a first aspect the present invention therefore relates to a *Solanum lycopersicum* plant comprising a pat-6 parthenocarpy gene. The pat-6 parthenocarpy gene is capable of conferring parthenocarpy to a *S. lycopersicum* plant. A pat-6 parthenocarpy gene of the invention is herein defined as a gene that is present on a DNA fragment that confers a parthenocarpy ratio of at least 10% in a *S. lycopersicum* plant of the cultivar Moneymaker when the plant is homozygous for the DNA fragment and is grown between April and July in the Netherlands in a greenhouse under controlled conditions (preferably as defined below herein), and wherein a) the DNA fragment is comprised within a segment of *S. habrochaites* chromosome 4 between markers TG182 and T0635; or, b) the DNA fragment hybridises to the complementary strand of the DNA fragment in a) under moderate, or preferably under stringent hybridisation conditions.

The parthenocarpy ratio as used throughout this specification is determined as described in the Examples herein whereby the *S. lycopersicum* plant of the cultivar Moneymaker with the pat and/or se genes of the invention is grown in green houses in the Netherlands under controlled conditions. Preferred controlled greenhouse conditions are: a minimum night temperature of 17° C.; a minimum day temperature of 19° C.; a relative humidity of about 75%; a daylength of about 16 hours; and, artificial light (150 µmol/m2/sec) starts when light levels are below 150 watt per square meter and ends when levels go over 250 watt per square meter. Spring and summer is herein defined as from April to July, winter is defined as from October to January.

A *S. lycopersicum* plant of the invention may be heterozygous for the pat-6 parthenocarpy gene but preferably the plant is homozygous for the pat-6 parthenocarpy gene.

A preferred *S. lycopersicum* plant of the invention comprises a *Solanum habrochaites* pat-6 parthenocarpy gene, more preferably a pat-6 gene as present in the *S. lycopersicum* IVT line-1, most preferably a pat-6 gene that originates from *S. habrochaites* LYC4. *S. habrochaites* LYC4 is available as, *L. hirsutum* LYC4 from the Mansfeld's World Database of Agricultural and Horticultural Crops IPK, Correstrasse 3, Gatersleben, Germany (mansfeld.ipk-gatersleben.de/). Seeds of the *S. lycopersicum* IVT-1 line were deposited under the Treaty of Budapest on 19 Oct. 2007 at NCIMB, Aberdeen, UK (www.ncimb.com) and were assigned accession no. NCIMB 41509.

In a second aspect the present invention relates to a *S. lycopersicum* plant comprising a pat-7 parthenocarpy gene. The pat-7 parthenocarpy gene is capable of contributing to the parthenocarpy phenotype of a *S. lycopersicum* plant comprising a pat-6 gene. A pat-7 parthenocarpy gene of the invention is herein defined as a gene that is present on a DNA fragment that confers an increase of at least 10% in parthenocarpy ratio in a *S. lycopersicum* plant of the cultivar Moneymaker comprising a *S. habrochaites* LYC4 pat-6 gene when the plant is grown between April and July in the Netherlands in a greenhouse under controlled conditions as herein defined above, and wherein a) the DNA fragment is comprised within a segment of *S. habrochaites* chromosome 5 between markers TG441 and TG538 and is linked to the marker CD64; or, b) the DNA fragment hybridises to the complementary strand of the DNA fragment in a) under moderate, or preferably under stringent hybridisation conditions. Preferably, linkage of the DNA fragment to the marker CD64 is herein defined as that the DNA fragment is within one centiMorgan above (telomeric) or below (centromeric) of the marker CD64 in a F2 population of which the F1 plant is a hybride between one parent that contains a *S. habrochaites* segment no larger than between markers TG441 and TG538 in a *S. lycopersicum* background crossed with a *S. Lycopersicum* plant that contains no *S. habrochaites* DNA or other wild DNA.

An increase in parthenocarpy ratio of at least 10% is herein understood to mean an increase of the parthenocarpy ratio of 4.1% to at least 4.51% in a pat-6 plant that does not or does comprise a pat-7 gene, preferably a single pat-7 gene, i.e. heterozygous (see e.g. Table 3 herein). Preferably the increase in pat-6 parthenocarpy ratio contributed by a pat-7 gene is at least 15, 20, 30, or 50% up to a maximum of a parthenocarpy ratio of 100%.

A *S. lycopersicum* plant of the invention may be heterozygous for the pat-7 parthenocarpy gene but preferably the plant is homozygous for the pat-7 parthenocarpy gene.

A preferred *S. lycopersicum* plant of the invention comprises a *S. habrochaites* pat-7 parthenocarpy gene, more preferably a pat-7 gene as present in the *S. lycopersicum* IVT line-1, most preferably a pat-7 gene that originates from *S. habrochaites* LYC4.

In a third aspect the invention pertains to a *S. lycopersicum* plant that comprises a pat-6 gene as well as a pat-7 gene, both as defined herein above. The plant may be heterozygous for either or both of the pat-6 and pat-7 genes. However, preferably the plant is homozygous for both the pat-6 and pat-7 genes.

In a fourth aspect the present invention therefore relates to a *S. lycopersicum* plant comprising a pat-8 parthenocarpy gene. The pat-8 parthenocarpy gene is capable of conferring parthenocarpy to a *S. lycopersicum* plant that also comprises a pat-9 parthenocarpy gene as defined below. A pat-8 parthenocarpy gene of the invention is herein defined as a gene that is present on a DNA fragment that confers a parthenocarpy ratio of at least 29% in a *S. lycopersicum* plant of the cultivar Moneymaker when the plant is homozygous for the DNA fragment and comprises a *S. habrochaites* pat-9 gene as present in the *S. lycopersicum* IVT line-1 and is grown between April and July in the Netherlands in a greenhouse under controlled conditions as herein defined above, and wherein a) the DNA fragment is comprised within a segment of *S. habrochaites* chromosome 4 between markers T0635 and TG287, preferably between markers T0958 and CT258; or, b) the DNA fragment hybridises to the complementary strand of the DNA fragment in a) under moderate, or preferably under stringent hybridisation conditions.

A *S. lycopersicum* plant of the invention may be heterozygous for the pat-8 parthenocarpy gene but preferably the plant is homozygous for the pat-8 parthenocarpy gene.

A preferred *S. lycopersicum* plant of the invention comprises a *S. habrochaites* pat-8 parthenocarpy gene, more preferably a pat-8 gene that originates from *S. habrochaites* LYC4, most preferably a pat-8 gene as present in the *S. lycopersicum* IVT line-1.

In a fifth aspect the present invention therefore relates to a *S. lycopersicum* plant comprising a pat-9 parthenocarpy gene. The pat-9 parthenocarpy gene is capable of conferring parthenocarpy to a *S. lycopersicum* plant that also comprises a pat-8 parthenocarpy gene as defined above. A pat-9 parthenocarpy gene of the invention is herein defined as a gene that is present on a DNA fragment that confers a parthenocarpy ratio of at least 65% in a *S. lycopersicum* plant of the cultivar Moneymaker when the plant is homozygous for the DNA fragment and comprises a *S. habrochaites* pat-8 gene as present in the *S. lycopersicum* IVT line-1 and is grown between April and July in the Netherlands in a greenhouse under controlled conditions as herein defined above, and wherein a) the DNA fragment is comprised within a segment of *S. habrochaites* chromosome 9 between markers TG1519 and At3g24010; or, b) the DNA fragment hybridises to the complementary strand of the DNA fragment in a) under moderate, or preferably under stringent hybridisation conditions.

A *S. lycopersicum* plant of the invention may be heterozygous for the pat-9 parthenocarpy gene but preferably the plant is homozygous for the pat-9 parthenocarpy gene.

A preferred *S. lycopersicum* plant of the invention comprises a *S. habrochaites* pat-9 parthenocarpy gene, more preferably a pat-9 gene that originates from *S. habrochaites* LYC4, most preferably a pat-9 gene as present in the *S. lycopersicum* IVT line-1.

In a sixth aspect the invention pertains to a *S. lycopersicum* plant that comprises a pat-8 gene as well as a pat-9 gene, both as defined herein above. The plant may be heterozygous for either or both of the pat-8 and pat-9 genes. However, preferably the plant is homozygous for both the pat-8 and pat-9 genes. A preferred *S. lycopersicum* plant comprising *S. habrochaites* pat-8 and pat-9 parthenocarpy genes is a plant that is not the *S. lycopersicum* IVT line-1.

In a seventh aspect the invention pertains to a *S. lycopersicum* plant that comprises various combination of the pat-6, pat-7, pat-8 and pat-9 genes, each as defined herein above. Such plants may thus comprise a pat-6 gene in combination with a pat-8 and/or pat-9 gene or a pat-7 gene in combination with a pat-8 and/or pat-9 gene. More preferred are however plants comprising all four of the pat-6, pat-7, pat-8 and pat-9 genes. Such plants may be heterozygous for any of the pat-6, pat-7, pat-8 and pat-9 genes. Most preferred are however plants that are homozygous for all four of the pat-6, pat-7, pat-8 and pat-9 genes.

In an eighth aspect the invention pertains to a *S. lycopersicum* plant that comprises a se functional sterility gene. Functional sterility is herein understood as a phenotype characterized by viable pollen, but wherein natural pollination is strongly restricted due to deviations from the normal morphology and function of the flower. The se functional sterility gene is capable of conferring functional sterility, as procured by exserted stigma, to a *S. lycopersicum* plant. Functional sterility as procured by exserted stigma is determined herein by measuring the length of the anther and style of one flower per plant at pre-anthesis on the third cluster. Exserted stigma was calculated by subtracting the anther length from the length of the style. *S. habrochaites* flowers have exserted stigmas, whereas the stigma of *S. lycopersicon* flowers is inside the anther cone at pre-anthesis. *S. lycopersicon* plants that are homozygous for the se gene produce flowers with stigmas significantly more exerted than heterozygous or homozygous SL plants (see e.g. Table 5). In *S. lycopersicon* plants that are homozygous for the se gene the stigmas are exserted by at least 1.0, 1.2, 1.5, or 2.0 mm.

A se functional sterility gene of the invention is herein defined as a gene that is present on a DNA fragment that confers functional sterility as procured by stigma that exsert by at least 1.0, 1.2, 1.5, or most preferably 2.0 mm in a *S. lycopersicum* plant of the cultivar Moneymaker when the plant is homozygous for the DNA fragment, and wherein: a) the DNA fragment is comprised within a segment of *S. habrochaites* chromosome 4 between markers TG538 and T358 and is linked to the marker TG318; or, b) the DNA fragment hybridises to the complementary strand of the DNA fragment in a) under moderate, or preferably under stringent hybridisation conditions.

A *S. lycopersicum* plant of the invention may be heterozygous for the se functional sterility gene but preferably the plant is homozygous for the se functional sterility gene.

A preferred *S. lycopersicum* plant of the invention comprises a *S. habrochaites* se gene, preferably as present in the *S. lycopersicum* IVT line-1, more preferably a *S. habrochaites* se gene that originates from *S. habrochaites* LYC4.

In a nineth aspect the invention pertains to a *S. lycopersicum* plant that comprises a se functional sterility gene as herein defined above, in combination with any of the various combinations of the pat-6, pat-7, pat-8 and pat-9 genes as described herein above. Such a *S. lycopersicum* plant may be heterozygous for the se functional sterility gene but preferably the plant is homozygous for the se functional sterility gene.

In another aspect the invention relates to a *S. lycopersicum* plant wherein any of the parthenocarpy and/or functional sterility genes are combined with one more of the additional genes for parthenocarpy and/or sterility, preferably functional sterility and/or positional sterility. The one or more additional genes for parthenocarpy or sterility may be previously described genes, including e.g. genes selected from the group consisting of pat, pat-1, pat-2, pat-3, pat-4, pat-5, ps-2, sha, and sds (see U.S. Pat. No. 6,060,648 and EP 1428425 for a description of the sources for these genes).

A *S. lycopersicum* plant according to any one of the aspects of the invention as described herein above, may be a plant of any one of the following commercial tomato types: cherry, cocktail, mini plum, plum cocktail, plum, round, beef and a number of specialty types as described herein. Suitable examples of tomato varieties or cultivars for each of these types are:

cherry: Claree, Conchita, Gisela, Favorita, Josefina, Lupita;
cocktail: Prolyco, Lycanto, Amoroso, WS4176, Aranca, Campari, Shiren, Panarea, Tyty;
mini plum: Santa, Santalina, Santella, WS4166, Dasher;
plum cocktail: Ginko, Balerina, Sunstream;
plum: Romana, Savantas, WS4178, WS4179, Reconquista, Recova, Yoga, Torro, Yaki;
round: Durinta, Habana, Plaisance, Mecano, Tricia, Grandella, Bizarr, Brilliant, Axxion, Ingar, Espero, Cedrico, Emotion, Daniela, Aromata, Clotilde, Ever, Clarance, Letitia, Ikram, Boludo, Astona;
beef: Bravona, Benevita, Delikata, Admiro, Prego, Growdena, Birloque, Quest, Macarena, Carson, Rapsodi, Cunero;
specialties: Kumato, Momotaro, Exota, Rosy, Yellow Gold, Orama, Carovita, Vintage.

Thus, a preferred *S. lycopersicum* plant according to any one of the aspects of the invention as described herein above is a plant of a cultivar selected from the group consisting of Claree, Conchita, Gisela, Favorita, Josefina, Lupita, Prolyco, Lycanto, Amoroso, WS4176, Aranca, Campari, Shiren, Panarea, Tyty, Santa, Santalina, Santella, WS4166, Dasher, Ginko, Balerina, Sunstream, Romana, Savantas, WS4178, WS4179, Reconquista, Recova, Yoga, Torro, Yaki, Durinta, Habana, Plaisance, Mecano, Tricia, Grandella, Bizarr, Brilliant, Axxion, Ingar, Espero, Cedrico, Emotion, Daniela, Aromata, Clotilde, Ever, Clarance, Letitia, Ikram, Boludo, Astona, Bravona, Benevita, Delikata, Admiro, Prego, Growdena, Birloque, Quest, Macarena, Carson, Rapsodi, Cunero, Kumato, Momotaro, Exota, Rosy, Yellow Gold, Orama, Carovita, and Vintage.

A *S. lycopersicum* plant of the invention is herein understood to be a plant of the *Solanum Lycopersicum* complex. The *Solanum Lycopersicum* complex includes, in addition to the cultured tomato *S. lycoperisicum*, various wild tomatoes such as *S. chmielewskii*, *S. habrochaites*, *S. pimpinellifolium*, *S. neorickii*, and *S. pennellii*, all of which are excellent for hybridisation with *S. lycoperisicum*. Tomato plants and tomato fruits of the *Solanum Lycopersicum* complex, are easily cross-bred with each other.

A preferred *S. lycopersicum* plant of the invention is a plant that comprises at least one of a pair of pat-6 and pat-7 genes and a pair of pat-8 and pat-9 genes, whereby preferably the plant is homozygous for at least one of the two genes in the pair, more preferably the plant is homozygous for both genes in the pair. Such a plant is capable of producing seedless tomatoes, preferably substantially seedless tomatoes as herein defined below. The plants of the invention, preferably produce (substantially) seedless tomatoes in a parthenocarpy ratio of at least 40, 50, 60, 70, 80, 90, 95, 97, 98, 99, 99.9 or a 100% in a wide variety of environmental conditions. This wide variety of environmental conditions is herein understood to include those environmental conditions under which tomato plants are generally known to be cultured and to set fruit. Such conditions include average day temperatures ranging from 8-40° C., preferably 12-35° C., night temperatures ranging from −2-30° C., preferably 0-28° C., a photoperiod per 24 hour period ranging from 4-20 hours, preferably 6-18 hours and an average humidity ranging from 10-100%, preferably 20-95%. The plants of the invention preferably at least produce seedless tomattoes in the aforementioned parthenocarpy ratio's when grown between April and July in the Netherlands in a greenhouse under controlled conditions as herein defined above.

Besides the parthenocarpic phenotype the plants of the invention further may comprise one or more of a number of predetermined properties which are desired for breeding, cultivating and/or growing tomato plants, and/or for the tomatoes produced by such plants. These properties are not specifically limited and for example comprise early fruit development, increased growth, increased production, any form of the plant or fruit (including round, cylindrical, pear or cherry), the size and/or quality of the fruit, the uniformity thereof, increased resistance against virusses or other diseases, increased cold resistance, long shelf life, etc., as will be clear to the person skilled in the art.

In another aspect the invention relates to relates to cultivation material for tomatoes such as seed or seedlings (optionally in a container) from any of the *S. lycopersicum* plants as herein defined above, and/or suited for use in the method(s) described herein. For some of the parthenocarpic and/or functionally sterile plants of the invention plants it may be impossible or inefficient to obtain seed by an essentially biological process and human intervention will be required for pollination and/or fertilisation. This human intervention generally comprises fertilizing the pre-embryo's of the flower of a first parent plant, with pollen obtained from the same or a second parent, respectively, dependent upon the choice of the father and the mother. It may be necessary to provide pollen by opening the pollen tube, by machine or preferably by hand, in practice by cutting or scissoring the pollen tube. For these and other situations the pollen is removed from the pollen tube, preferably again by hand, for instance by scraping, after which the pollen thus obtained is applied to the flower/pistil of the mother plant, again preferably by hand, such as by brushing or another suitable manner, such as spraying, to fertilize the (pre-embryo's of the) mother plant. Manual pollination is a commonly used technique for obtaining hybrid tomatoes, to which for the purposes of the invention only the opening and scraping of the pollen tubes has to be added.

In yet a further aspect the invention relates to (a) fruit from a *S. lycopersicum* plant as defined herein above. Preferably the fruit is a seedless fruit, i.e. a seedless tomato. As used herein, the term "seedless tomato" refers to a tomato that does not contain any fertilized mature seeds. While the tomatoes of the present invention do not contain any fertilized mature seeds, the tomatoes may contain unfertilized ovaries, which are small and white in color. These unfertilized ovaries are not considered to be true seeds. The seedless tomatoes of the present invention are substantially seedless. As used herein, the term "substantially seedless" means that the tomato is at least 90% seedless. Preferably, the seedless tomatoes of the present invention are about 95% to about 99% seedless, most preferably, the tomatoes of the present invention are about 100% seedless.

In further aspects the invention relates to methods for producing plants and tomatoes as herein defined above.

In a first such aspect the invention thus relates to a method for producing a *S. lycopersicum* plant that is homozygous for at least one of the pat-6, pat-7, pat-8, pat-9 and se genes as herein defined above. The method preferably comprises the steps of: a) crossing a first *S. lycopersicum* plant with a second plant of the *Solanum Lycopersicum* complex that comprises at least one of the pat-6, pat-7, pat-8 and pat-9 and se genes; b) backcrossing the F1 generation and further generations for at least two generations with the first *S. lycopersicum* plant as recurrent parent; and, c) selfing the furthest backcrossed generation obtained in b) for at least two generations. Preferably in the method at least one molecular marker is used in at least one of steps b) and c) to select for a *S. lycopersicum* plant that is homozygous for at least one of the pat-6, pat-7, pat-8, pat-9 and se genes.

In a second such aspect the invention relates to a method for producing a *S. lycopersicum* plant that produces seedless tomatoes as herein defined above. The method preferably comprises the steps of: a) crossing a first *S. lycopersicum* plant with a second plant of the *Solanum Lycopersicum* complex that comprises at least one of the pat-6, pat-7, pat-8 and pat-9 genes; b) backcrossing the F1 generation and further generations for at least two generation with the first *S. lycopersicum* plant as recurrent parent; and, c) selfing the furthest backcrossed generation obtained in b) for at least two generations. Preferably in the method at least one molecular marker is used in at least one of steps b) and c) to select for a *S. lycopersicum* plant as defined herein above. a *S. lycopersicum* plant that produces seedless tomatoes as herein understood to mean a plant that is capable of producing seedless tomatoes and that preferably does produce seedless tomatoes under environmental conditions as herein defined above.

A "molecular marker" is herein understood to refer to a nucleic acid sequence, or a set thereof, that is indicative (directly or indirectly) for the presence or absence of a particular allele, e.g. an allele of a pat-6, pat-7, pat-8, pat-9 and se gene as herein defined. The presence or absence of the molecular marker can be detected in a wide variety of molecular assays or tests. These laboratory-based techniques available for the analysis, comparison and characterization of plant genotypes at the molecular level include e.g. Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) which are also referred to as Microsatellites, and Single Nucleotide Polymorphisms (SNPs).

The exact type of assay developed is not important, as long as it can discriminate between an allele of a pat-6, pat-7, pat-8, pat-9 and se gene as herein defined on the one hand and corresponding *S. lycopersicum* allele on the other hand Examples of various types of assays are given in the Examples. In order to perform the marker-assisted selection in the methods of the present invention, the subject tomato plants or plant parts are, for example, first subjected to DNA extraction, the techniques of which are known in the art (See Hnetkovsky et al., Crop Sci., 36(2): 393-400 (1996)). Once the extraction is complete, a molecular assay can be performed, including, but not limited to, a cleaved amplified polymorphic sequence (CAPS) assay (see Akopyanz et al., Nucleic Acid Research, 20:6221-6225 (1992) and Konieczny & Ausubel, The Plant Journal, 4:403-410 (1993)) or a SCAR assay. A SCAR assay involves amplifying DNA at the locus (e.g. a specific locus near one of the pat-6, pat-7, pat-8, pat-9 and se genes of the invention) by PCR followed by digestion with restriction enzymes. Polymorphisms between the nucleic acid sequences differentiates between different alleles by resulting for example in different sized restriction fragments. Examples of nucleic acid primers and enzymes employed in these assays are given in the Examples herein.

Thus, in a preferred method of the invention, the molecular marker is selected from the group consisting of markers that are linked to or that are diagnostic for the presence of: a) a segment of *S. habrochaites* chromosome 4 between markers TG182 and T0635; b) a segment of *S. habrochaites* chromosome 5 between markers TG441 and TG538; c) a segment of *S. habrochaites* chromosome 5 that is linked to the marker CD64; d) a segment of *S. habrochaites* chromosome 4 between markers T0635 and TG287; e) a segment of *S. habrochaites* chromosome 4 between markers T0958 and CT258; f) a segment of *S. habrochaites* chromosome 9 between markers TG1519 and At3g24010; g) a segment of *S. habrochaites* chromosome 5 between markers TG538 and TG358; and, h) a segment of *S. habrochaites* chromosome 5 that is linked to the marker T318. More preferably the molecular marker is selected from the group consisting of markers TG182, T0891, T0958, T0635, 114C15-S, TG609, SSR450, SSR94, CT258, TG441, CD64, TG538, At3g24010, T0156, SSR599, At5g06360, T1065, CT220, TG358 and T318.

In a further aspect the invention relates to the use of a molecular marker as defined above for marker assisted breeding of a *S. lycopersicum* plant capable of carrying seedless tomatoes.

In a further aspect, the invention relates to a method for producing a seedless tomato. The method preferably comprises cultivating a plant as defined herein above, or a plant obtained or obtainable by a method as herein defined above, under conditions conducive to the production of seedless tomatoes, and optionally harvesting the tomatoes. Conditions conducive to the production of seedless tomatoes are also defined herein above. The seedless tomatoes produced on the plants of the invention can be harvested and marketed and/or consumed as such, or optionally after one or more further processing steps, such as sorting, washing or packaging.

The seedless tomatoes according to the invention can also be processed further in a manner known per se to tomato products, in particular food products, which may or may not be in a form ready or suited for final use. In this respect, the tomatoes according to the invention have the advantage that they can be processed directly, without a further step for removing the seeds/pips in the production process.

The invention in a further aspect therefore relates to products, in particular food products, obtained from the seedless tomatoes according to the invention, as well as to a method for obtaining said food products, in which the tomatoes are processed to these products without a separate step for removing the seeds. Such a method can therefore—inter alia—comprise puréeing or mashing in another way of the tomatoes, optionally followed by incorporating or adding further desired ingredients, and packaging the tomato product thus obtained, without seeds or the residues thereof, in suitable containers for storage, transport or sale, in which said method does not comprise a step for removing any pips/seeds between the mashing of the tomatoes and the packaging of the product.

For such final use, another advantage of the seedless tomatoes of the invention is that they will have a higher content of fruit flesh (expressed as dry weight) compared to non-seedless tomatoes harvested at a corresponding time, i.e. 1, 2, 5, 10, 25, or 35%, or more, based on total weight of the tomato (i.e. on average about 5.5 to 6.5 gram dry matter for the seedless tomatoes compared to about 4.5 to 5.5 gram dry matter for non-seedless tomatoes, on a total weight at harvest of about 110-120 gram). In terms of dry matter yield, this means an increase of at least about 20% (in which furthermore the dry matter of the non-seedless tomatoes will still include the pips).

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

EXAMPLES

1. Materials and Methods 1.1 Plant Materials

Figure 6:
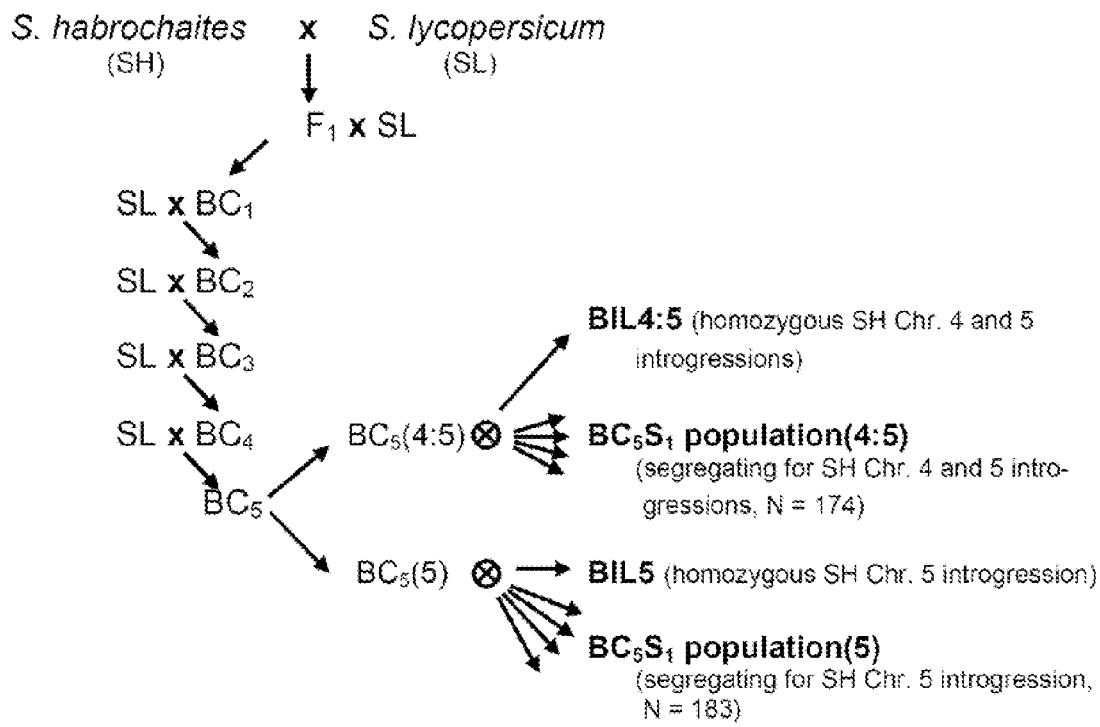
FIG. 6: Backcross program resulting from an interspecific cross between S. habrochaites LYC4 (SH) and S. lycopersicum cv. Moneymaker (SL) for the development of BIL4:5, BIL5, $BC_5S_1$ population(4:5) and $BC_5S_1$ population(5).

For the mapping of parthenocarpy genes in Solanum habrochaites LYC4, we originally used two $BC_5S_1$ populations that were part of the introgression line (IL) development program of Finkers et al. (2007b) (see FIG. 6). These ILs contain chromosome fragment(s) of Solanum habrochaites LYC4, hereafter referred as SH, in a Solanum lycopersicum cv. Moneymaker genetic background, hereafter referred as SL. The two $BC_5S_1$ populations had previously been used for the selection of IL 5-1 and IL 5-2 (Finkers et al, 2007b) and will be hereafter denoted as populations 5-1 and 5-2. Population 5-1, segregating for the short arm of Chromosome 4 and the entire Chromosome 5, consisted of 174 plants. Population 5-2, segregating for the long arm of Chromosome 5, was composed of 183 plants. Plants were grown in greenhouse in The Netherlands under controlled conditions. Subsequently a set of relevant $BC_5S_2$ recombinant plants were selected and further studied.

For the mapping of parthenocarpy genes in IVT-line 1, we used an $F_2$ population coming from a single cross between IVT-line 1, parthenocarpic, and Solanum lycopersicum cv.

Moneymaker, not parthenocarpic. The $F_2$ population was composed of 160 plants and grown under controlled conditions in greenhouses in The Netherlands. Seeds of the *S. lycopersicum* IVT-line 1 were deposited under the Treaty of Budapest on 19 Oct. 2007 at NCIMB, Aberdeen, UK (www.ncimb.com) and were assigned accession no. NCIMB 41509.

1.2 Flower Morphology

Fresh flowers were collected and analyzed at pre-anthesis on the third cluster of $BC_5S_1$ plants. Anther length and style length were measured to the nearest 0.1 mm using an ocular reticle.

1.3 Characterization of Parthenocarpy

To minimize pollination, in order to promote parthenocarpy, plants were not vibrated. To classify the level of parthenocarpy, the first five clusters of a plant were analyzed for fruit size, number of fruits per cluster, number of flowers per cluster and the presence of seeds. The size of the fruits was measured with the use of an ocular reticle to the nearest 1 mm. Fruits were scored at mature stage. The trait parthenocarpy was calculated quantitatively, as the percentage of seedless fruits from the total number of flowers per cluster. Subsequently we calculated the average percentage of seedless fruit set per plant, over the first five clusters.

1.4 DNA Extraction

Two DNA isolation techniques were used. For most experiments total DNA was isolated from two young tomato leaves by using a rapid CTAB DNA isolation method as described by Steward and Via (1993), adjusted for 96-well format using 1.2 ml COSTAR cluster tubes (Corning Incorporated). Leaf samples were crushed using a Retsch.

DNA isolation, for the selection of relevant $BC_5S_2$ progenies, was performed by a rapid alkaline (NaOH) based extraction method (Wang et al. 1993). This method was up-scaled to a 96-well format as described by Gorguet et al (2006).

1.5 Molecular Marker Analysis

Genotypes were determined using PCR-based markers. Primers and enzymes of CAPS and SCAR markers TG441, CD64, CD31, TACL2, TG538, TG318 and TG358 have been described by Coaker & Francis (2004), and Brouwer & St. Clair (2004). Other CAPS and SCAR markers were generated based on RFLP and COS marker sequences previously mapped by Tanksley et al. (1992) or Fulton et al. (2002). The sequences of the RFLP and COS markers were available on the "SOL Genomics Network" (Mueller et al. 2005; sgn.cornell.edu). The conversion of RFLP and COS markers into CAPS and SCAR markers was performed as described in Gorguet et al (2006). See table 1. Each PCR reaction (25 µl) contained 10-20 ng of genomic DNA, 1×PCR-reaction buffer, 0.4 µM of each forward and reverse primer, 0.2 mM dNTPs and 0.5 unit Taq polymerase in demi water. PCR conditions were: hot start of 5' at 94° C., followed by 39 cycles of 30" at 94° C. 30" at annealing temperature (Table 1), 30" at 72° C. and a final extension of 7' at 72° C. About 3 µl of PCR product was digested in a total volume of 15 µl for at least 3 h with 1-2 unit of restriction enzyme. After digestion, DNA fragments were separated on a 2-3% agarose gel.

Reverse primers for microsatellites markers were labeled with IRD700 or IRD800. PCR reactions (10 µl) were prepared in the same proportion as described for CAPS markers, only with 0.1 µM forward and labeled reverse primer. PCR conditions were: hot start of 3' at 94° C., followed by 30 cycles of 45" at 94° C., 45" at 53° C., 1' at 72° C. and a final extension of 3' at 72° C. After the PCR, 10 µl LI-COR loading dye was added and the IRD700 labeled fragments were analyzed on a LI-COR 4200 DNA sequencer, essentially following the method published by Myburg and Remington (2000).

AFLP markers were determined as described by Gorguet et al. (2006).

1.6 Data Analysis and Mapping

To normalize the distribution of the recorded trait, the percentages of seedless fruits were transformed to a logit scale: logit (p)=log(p/(100−p)), (with p the percentage of seedless fruits on the first five clusters per plant).

Genetic linkage maps were constructed with JoinMap 3.0 (Van Ooijen and Voorrips 2001), applying the Kosambi mapping functions. QTL mapping was performed using the interval mapping and multiple-QTL mapping procedures of MapQTL 5 (Van Ooijen 2004). A logarithm of odds (LOD) threshold value of 3.0 was set (Van Ooijen 1999). A two-LOD support interval was taken as a confidence interval for a putative QTL.

Models for QTL analysis are presented hereafter.

In the $BC_5S_2$ population, the linear model used for the phenotype Y of an individual was:

$$Y_{i(j)} = \mu + X_{i(j)} \alpha^j + e_i \quad [1]$$

where µ is the population mean, $X_{i(j)}$ is the number of SH alleles at the major locus for individual i(j) and $\alpha_j$ is the effect of one allele of the major gene. This effect differs according to j, the genotypic status of the minor gene. j=1 (i=1 . . . 61) when the minor gene is homozygous SL; j=2 (i=1 . . . 21) when the minor gene is heterozygous and j=3 (i=1 . . . 24) when the minor gene is homozygous SH. $e_i$ is the residual.

In the $F_2$ population used for the mapping of two parthenocarpy genes, the model used for the phenotype Y of an individual was the factorial combination of the two loci:

$$Y = \mu + X_1 X_2 + e \quad [2]$$

Where µ is the population mean, $X_1 X_2$ is the effect of the combinations of the two parthenocarpy genes and e is the residual.

2. Results 2.1.1 Mapping of Parthenocarpy Genes in *S. Habrochaites* Lyc4

Parthenocarpic fruit development was observed in the introgression line IL5-1 developed by Finkers et al (2007b). IL5-1 carries an SH introgression on the short arm of Chromosome 4 and the complete Chromosome 5 from SH. In addition, flowers of IL5-1 presented an exerted style from pre-anthesis stage on, which partly prevented altered self-pollination. We hypothesed that parthenocarpy in IL5-1 was due to a combination of parthenocarpy gene(s) and positional sterility. Because ILs were initially vibrated to promote pollination, parthenocarpic fruit development was only obvious with the presence of a certain form of sterility. IL5-2, carrying only the long arm of Chromosome 5 of SH was not parthenocarpic but showed style exertion. The conclusion was that the gene responsible for style exertion is located on Chromosome 5.

To map and characterize the parthenocarpy and positional sterility genes observed in this material, we generated a genetic linkage map of the introgressed regions of the two ILs by making use of two $BC_5S_1$ populations: population 5-1 and population 5-2 segregating for the SH introgressions of IL5-1 and IL5-2 respectively. Both populations were screened in a juvenile stage with SCAR marker TG318, to select for plants with a homozygous or heterozygous SH introgression on Chromosome 5. The final population 5-1 and population 5-2 consisted of 74 and 66 plants, respectively. TG318 was chosen to screen the population 5 due to its central position on Chromosome 5. Therefore by skipping the plants homozygous SL at TG318 locus on Chromosome 5, we enriched the population for plants with functional sterility to promote visible parthenocarpic fruit development. Subsequently, parthenocarpy was evaluated in population 5-1 and positional sterility in populations 5-1 and 5-2.

2.1.2 Genetic Linkage Map Construction

The initial step in the development of linkage maps in the regions of the SH introgressions was to identify markers on the borders of the introgression. We developed a set of RFLP- and COS-derived PCR primer combinations in the expected regions of the introgressions and determined whether the locus was in or out. The border of the introgression on Chromosome 4 in IL5-1 was determined between markers T0635 and TG609, respectively at 55 cM and 56 cM on the EXPEN2000 linkage map. On Chromosome 5, the border of the introgression in IL5-2 was identified between markers CD64 and CD31, respectively at 27 cM and 39 cM on the EXPEN1992 linkage map. IL5-1 is likely to cover the entire Chromosome 5 (Finkers et al, 2007b).

Figure 2:
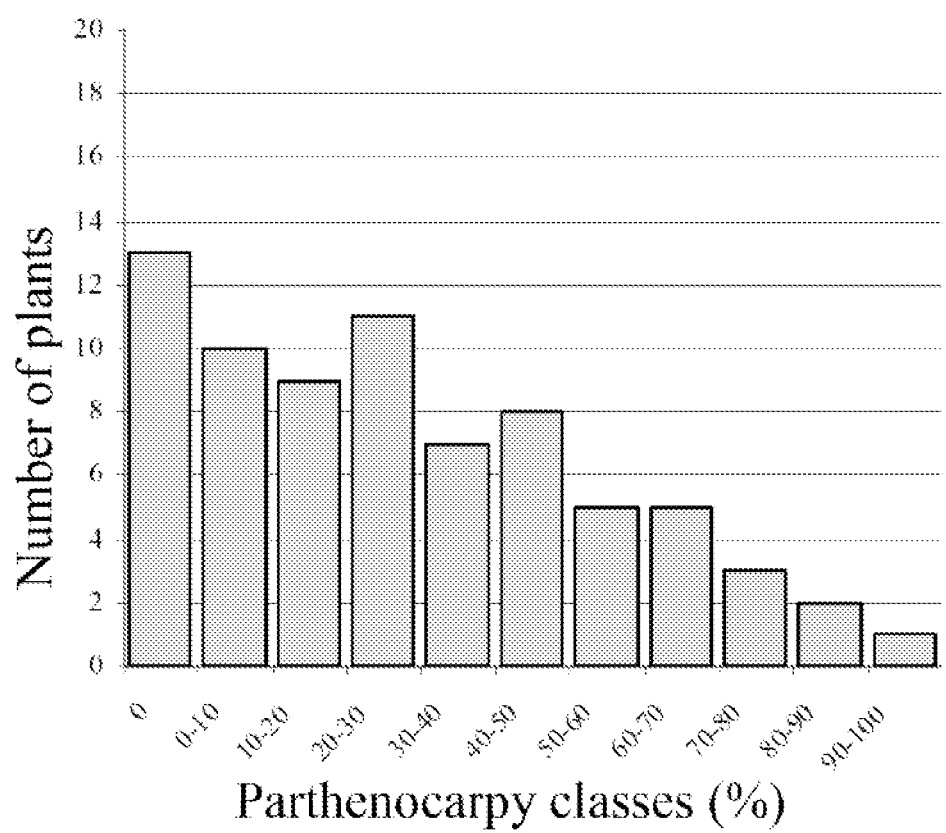
FIG. 2: Frequency distribution of the average percentage of seedless fruit set over the first five clusters in the BC5Si population 5-1 (n=74).

The genetic linkage map of the SH Chromosome 4 introgression of IL 5-1 was generated using the population 5-1 (n=74). Thirteen RFLP or COS markers located on the short arm of Chromosome 4 in the EXPEN2000 map were converted into CAPS or SCAR markers and mapped in population 5-1. Two microsatellite markers, SSR43 and SSR72 (sgn.cornell.edu; Mueller et al. 2005), were added. The introgression on Chromosome 4 spanned 22.4 cM which is almost the complete short arm of Chromosome 4, from the telomere to CAPS marker T0635. (FIG. 2).

The genetic linkage map of the SH Chromosome 5 was constructed using populations 5-1 and 5-2. A total of nine CAPS or SCAR markers were developed either based on available information (Coaker and Francis 2004; Brouwer and St. Clair 2004) or based on the RFLP sequence (Tanksley et al. 1992). The SH introgression of IL5-2 spanned 26.2 cM on the long arm of Chromosome 5, from the telomeric end to CAPS marker CD31. The limit of the SH introgression of IL5-1 on the short arm of Chromosome 5 (distal to TG441), was not determined, therefore the introgression spanned at least 57.4 cM. (FIG. 2).

The order of the markers on Chromosome 4 and 5 were in accordance with the Tomato-EXPEN2000 map and EXPEN1992 map of the "SOL Genomics Network" (sgn.cornell.edu). Overall the map distances in the Chromosome 4 and 5 introgressions were reduced by 58% compared to the EXPEN2000 reference map and 31% in the Chromosome 5 introgression (TG441-CT138) in comparison to the high-density RFLP tomato map (Tanksley et al. 1992).

2.1.3 Screening and Segregation of Parthenocarpy

Figure 1:
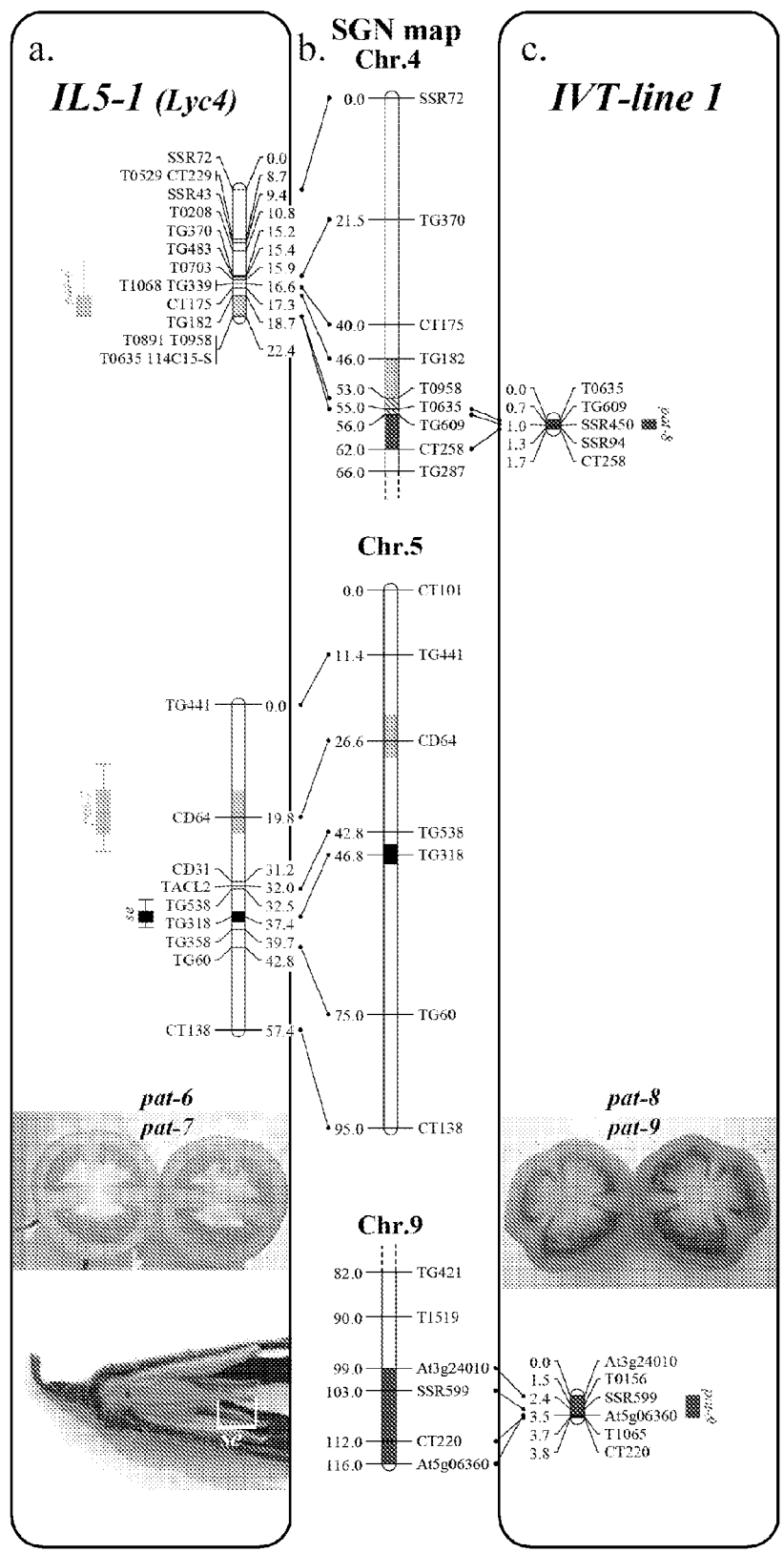
FIG. 1: (Panel A) Genetic linkage groups of Chromosome 4 and Chromosome 5 SH introgressions of IL5-1 developed on population 5-1 (BC5S1). The position of the parthenocarpy QTLs (pat-6 and pat-7) is indicated in red on the left of the linkage map. pat-6 was mapped in the BC5Si population and pat-7 in the BC5S2 population. The location of the style exertion locus (se) is indicated in black. The QTL bars indicate an interval in which the inner, thicker bar, shows a one LOD support confidence interval and the outer bar, thinner, shows a two LOD support confidence interval. (Panel B) SGN reference map for the short arm and centromeric region of Chromosome 4, the complete Chromosome 5 and the telomeric region of the long arm of Chromosome 9 (hsgn.cornell.edu). The putative positions of the identified QTLs is represented by respective color codes. Because the one LOD confidence interval of pat-6 and pat-7 are overlapping, this overlap is indicated with dashed black lines. (Panel C) Genetic linkage groups of Chromosome 4 and Chromosome 9 SH introgressions of IVT-line 1 developed on the $F_7$ population. The position of the parthenocarpy QTLs (pat-8 and pat-9) is indicated in brown. Map positions are given in cM. The pictures represent the phenotypic aspect of the measured traits. Maps and QTL alignments were performed with MapChart.

Parthenocarpy was characterized quantitatively, as the percentage of seedless fruits in the first five clusters over the total number of flowers in those clusters. (FIG. 1). The distribution of the parthenocarpy level ranged from 0 to 90.5% and the average size of the parthenocarpic fruits (4.73 cm) did not significantly differ (P>0.05) from the size of the seeded fruits (4.75 cm).

2.1.4 Mapping of the Parthenocarpy Locus

To improve the normality of the parthenocarpy ratio, this percentage was transformed into a logit scale and this last parameter was used for the QTL mapping procedure. By applying Interval Mapping, one QTL for parthenocarpy (designated pat-6) was identified on Chromosome 4 (FIG. 2), close to the centromere, with the highest LOD value at CAPS markers T0958/T0891/T0635 (Table 2). This QTL explained 48.9% of the total variation. By using one of the three peak marker as cofactor, in an MQM mapping procedure, no extra QTL was detected.

Figure 3:
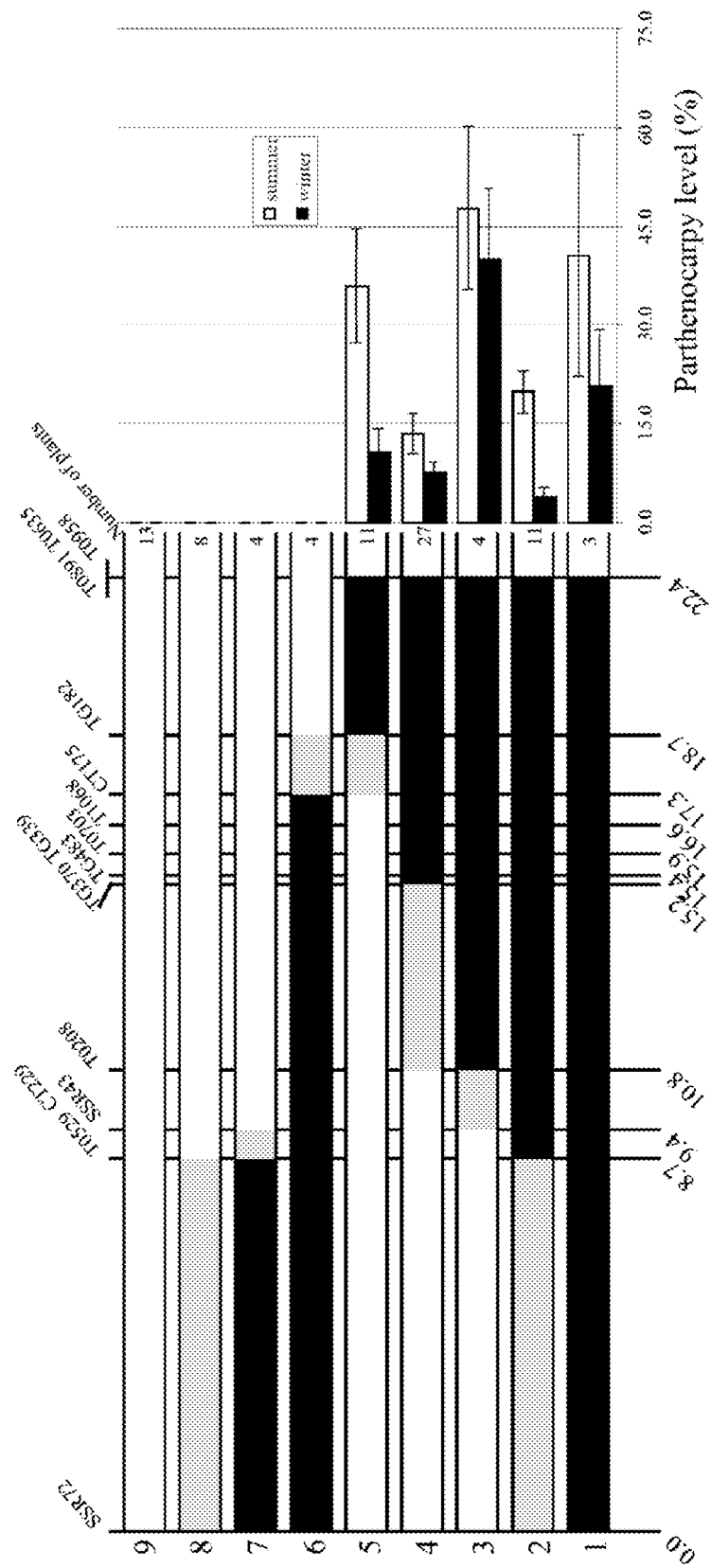
FIG. 3: Left: Graphical genotypes of $BC_5S_2$ progenies for the short arm of Chromosome 4. Color code: Back stands for homozygous SH, white for homozygous SL and grey for unknown because the exact position of the recombination between the two closest flanking markers is unknown. Numbers under the bars indicate the position of the above mentioned markers, in cM. The reference number of each progeny is indicated at the far left of the graphical genotypes and the number of plants per progeny at the far right. Right: Average parthenocarpy ratio over the first five clusters per specific progeny, in spring/summer (white) and winter (black), indicated with Standard Error bars.

2.1.5 Confirmation of Parthenocarpy Genes in $BC_5S_2$:

In order to confirm and narrow down the position of pat-6 on Chromosome 4 and to study the potential interaction of pat-6 with genes on Chromosome 5, we developed a set of recombinant progenies with small homozygous SH introgressions on the short arm of Chromosome 4. To develop this set of progenies, $BC_5S_2$ plants, recombinant for the Chromosome 4 introgression, were screened at seedling stage using molecular markers. Homozygous recombinant plants were selected and divided into 9 classes (FIG. 3). Potential parthenocarpy genes on Chromosome 5 could not be identified in the $BC_5S_1$ population because most plants were homozygous SH or heterozygous for Chromosome 5. The evaluation of the recombinant progenies segregating randomly for Chromosome 5 allowed us to look for potential parthenocarpy genes on Chromosome 5. Selected plants were genotyped and evaluated for level of parthenocarpy from April to July 2006 (hereafter referred as Spring/Summer). After making cuttings the recombinant progenies were grown and re-evaluated in winter 2006/2007. The level of parthenocarpy in each recombinant progeny is presented in FIG. 3. Only recombinant progenies carrying the SH chromosome segment TG182-T0635 produced parthenocarpic fruits. This narrows down the position of the parthenocarpy gene pat-6 to 3.7 cM in population 5.1. The parthenocarpy level was significantly higher in spring/summer than in winter (P<0.05). But more strikingly the level of parthenocarpy varied greatly from one progeny to another and this did not depend on the size of the SH fragment in, eliminating the possibility of having a second parthenocarpy gene on that chromosome. Therefore we investigated the potential interaction of pat-6 with Chromosome 5 in progenies 1 to 5. To study this interaction we applied the Multiple-QTL model (MQM) mapping function and used marker T0635 (one of the peak marker for pat-6) as cofactor. A QTL linked to marker CD64 on Chromosome 5 showed a significant effect on the expression of the parthenocarpy trait (FIG. 2). This QTL is hereafter referred as pat-7 and it was detected in both seasons.

In order to study the effects and interaction of pat-6 and pat-7 (Table 3), we searched for the best linear model to explain the observed variation. The pat-6 gene is clearly the main gene in this interaction, but the size of its effect depends on the alleles of the pat-7 locus. A higher level of parthenocarpy is observed when the two SH alleles of pat-6 are present in combination with at least one SH allele of pat-7. In spring/summer, the parthenocarpy ratio observed on these plants is in average of 41% with one SH allele of pat-7 and 46% with two SH alleles. When pat-6 is homozygous SL, the pat-7 gene alone never shows parthenocarpy. Regarding these two observations, model [1] was found as the best fitting linear model, with a coefficient of correlation of 64.8% in spring/summer and 57.9% in winter. The details of this model are given in table 4.

2.1.6 Characterization and Mapping of Functional Sterility

Functional sterility, procured by exerted stigma, was evaluated in populations 5-1 and 5-2 by measuring the length of the anther and style at pre-anthesis on the third cluster. The size of the exerted stigma was calculated by subtracting the anther length from the length of the style. SH flowers have exerted stigmas, whereas the stigma of SL flowers is inside the anther cone at pre-anthesis. Interval Mapping showed one major QTL for stigma exertion (se), on Chromosome 5 (FIG. 2) linked to marker TG318. Plants homozygous for the SH introgression at marker TG318 produced flowers with stigmas significantly more exerted than heterozygous or homozygous SL plants at that marker (LOD 19.2; Table 5).

Sterility was also characterized qualitatively in population 5-2 by determining the presence or absence of seeds. Plants with no seeded fruits over the five characterized clusters were differentiated from plants producing at least one seeded fruit. Population 5-1 was not used for this purpose, because this population was also segregating for parthenocarpy which influences the setting of seeded fruits. This trait co-segregated with CAPS marker TG318 on Chromosome 5 and thus with the QTL for stigma exertion.

2.2.1 IVT-Line 1

The IVT-line 1 has been developed from an interspecific cross between *Solanum habrochaites* (accession unknown) and SL, followed by several generations of back crosses followed by at least one selfing, in the early 1980's (Zijlstra, 1985). In a first step towards the mapping of the parthenocarpy gene(s) present in IVT-line 1 we wanted to identify the positions of the SH introgressions. We screened a large number of known *S. habrochaites* AFLP markers on IVT-line 1. Seven SH introgressions could clearly be identified, on Chromosomes 4, 5, 6, 9 and 11. Only introgressions where known *S. habrochaites* AFLP markers were present can potentially be retrieved, therefore we cannot exclude the possible presence of other, small SH introgressions.

Figure 4:
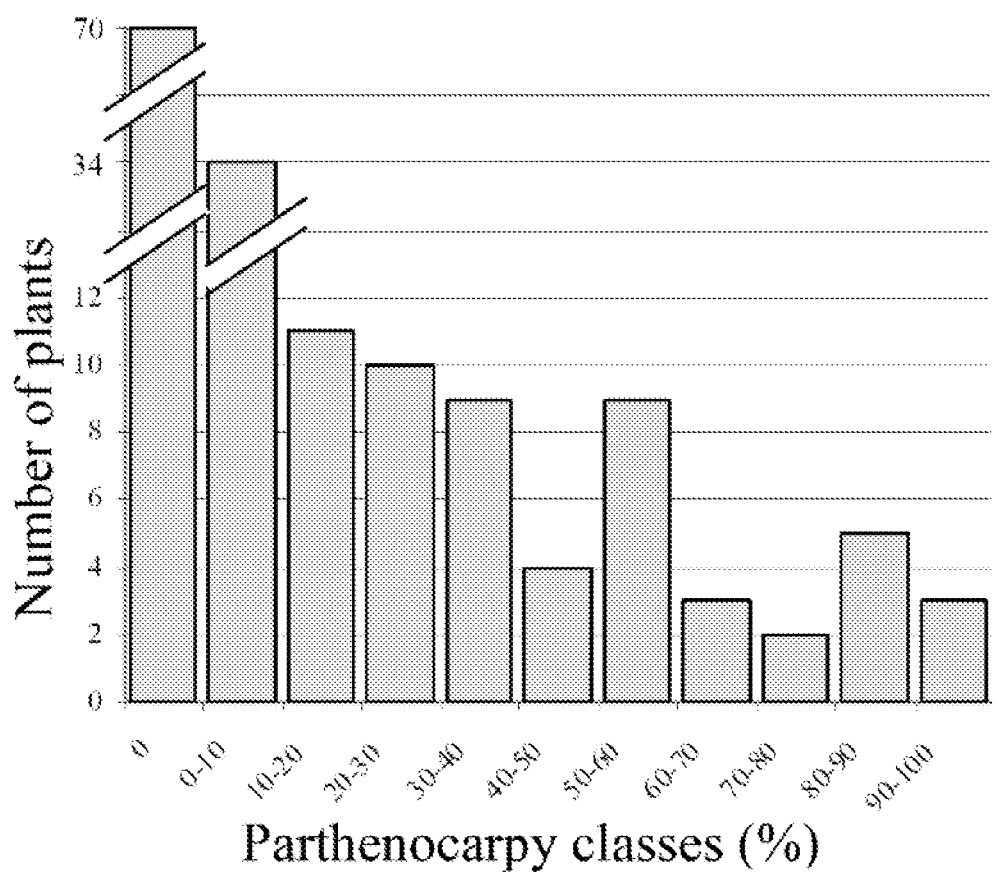
FIG. 4: Frequency distribution of the average percentage of seedless fruit set over the first five clusters in the $F_2$ population of IVT-line 1 (n=160).

An $F_2$ population composed of 160 plants, coming from the cross between IVT-line 1 and SL, was grown, and the parthenocarpy level of the plants was evaluated in spring 2006 in Wageningen, The Netherlands, following the same procedure as previously described. The parthenocarpy ratio in the $F_2$ population ranged from 0 to 97%, with 44% of the plants without any parthenocarpic fruit (FIG. 4). Seeded and seedless fruits within the same clusters were significantly different in size (P<0.05), with averages of 4.36 cm and 4.11 cm, respectively.

Because of the presence of an SH introgression around the centromere of Chromosome 4, where pat-6 was previously mapped, we hypothesized that parthenocarpy in IVT-line 1 might also be under the control of pat-6 or an allelic variant of it. After confirming that marker T0635 was in the SH introgression of IVT-line 1, we tested the association between marker T0635 (peak marker for pat-6) and the segregation of parthenocarpy observed in the $F_2$ population. This association was highly significant.

Although the association was significant it was clear that not all plants homozygous SH for T0635 produced parthenocarpic fruits, which may be due to the mode of action of another locus. To localize this other locus, we screened AFLP primer combinations on the set of $F_2$ plants homozygous SH at the T0635 locus. One AFLP marker, P18M51-219 was clearly associated with the parthenocarpy and was known to be located in the Chromosome 9 introgression. Parthenocarpy in IVT-line 1 is therefore under the control of at least two genes, one located near the centromere of Chromosome 4 and one near the telomere of the long arm of Chromosome 9.

To map these two parthenocarpy loci more accurately, we developed a linkage map for the introgressions on Chromosomes 4 and 9 (FIG. 2). The borders of the introgression on Chromosome 4 were between markers T0635 and T0958 and between CT258 and TG287. On Chromosome 9, the upper limit of the introgression was located between markers T1519 and At3g24010 and likely spanned the rest of the long arm of Chromosome 9. The two linkage groups were generated using eight CAPS markers, converted from RFLP or COS sequences and three SSR markers (SGN database; Mueller et al, 2005). The order of the markers on Chromosome 4 was identical as in the SGN reference map. In the introgression of Chromosome 9, few inversions of marker orders were observed. The introgression of Chromosome 4 spanned 1.7 cM (7 cM on the SGN reference map) and the introgression on Chromosome 9 was 3.8 cM (17 cM in the reference map). These means a suppression of recombination of about 75%.

Figure 5:
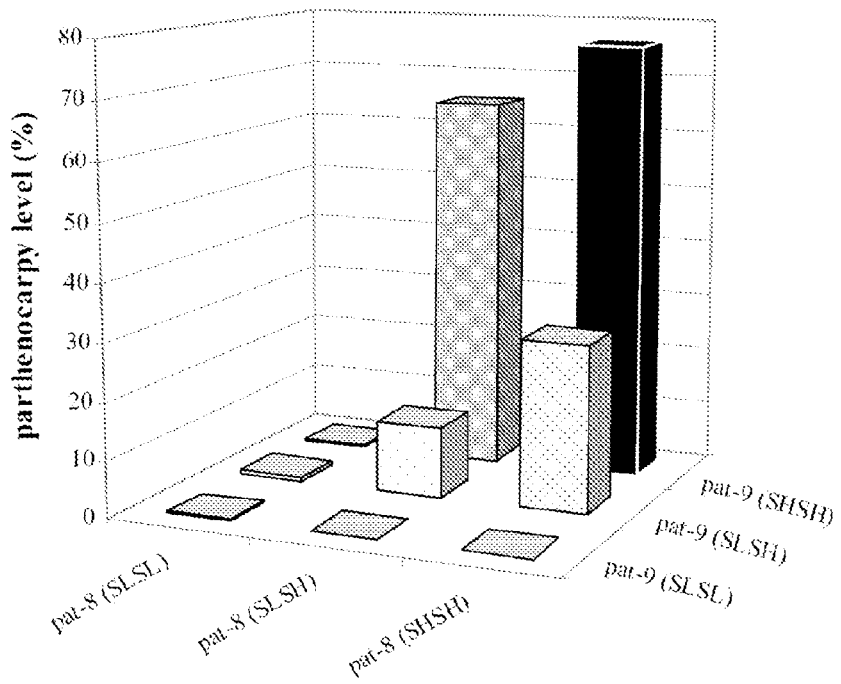
FIG. 5: Interaction between pat-8 and pat-9 in the F2 population (n=137). Each column stands for the average pat ratio per alleles combination recorded in spring (2006). Difference of colors between bars relate the significant differences between groups (P<0.05).

Parthenocarpy genes were mapped using MapQTL. We used a logit scale of the parthenocarpy ratio to improve the normality of the distribution. Because of the small genetic sizes of the two introgressions on Chromosomes 4 and 9, both complete regions were highly significant and it was not possible to narrow down the position of the two parthenocarpy genes. These two parthenocarpy genes are hereafter denoted as pat-8 and pat-9, respectively for the gene located on Chromosome 4 and Chromosome 9. Because it was not possible to narrow down the genetic regions in which pat-8 and pat-9 were located, we excluded the plants recombinant for one or both introgressions in the following analysis, and plants with an ambiguous scoring, in order to improve the accuracy of the calculations. In total, out of 160 $F_2$ plants, 137 were not recombinant for any of the two introgressions. An ANOVA showed that both loci had a highly significant effect on parthenocarpy and also the interaction between both loci was highly significant. Therefore we selected model [2] as the best fitting model to explain the observed variation in the $F_2$ population ($R^2$=73.7%). The observed and predicted effect, based on model [2], of the different allele's combinations between pat-8 and pat-9 is presented in FIG. 5 and table 6. The absence of SH allele in either of the pat-8 or pat-9 loci results in no parthenocarpic fruits. The highest level of parthenocarpy is obtained when both genes are homozygous SH (76% of parthenocarpic fruit set).

TABLE 1

Primer sequences and PCR reaction parameters for CAPS and SCAR markers

| Marker type | Name | Use | Primer (5'-3') $F_w$, $R_v$ | Size$^a$ (bp) | TA$^b$ (° C.) | Restriction enzyme | Chr$^c$ |
|---|---|---|---|---|---|---|---|
| CAPS | U241098 | ILs and IVT-1 | CTTAAAGGCACACTTAGATTCA CTGAGAATTCTCTTGACTGCA | 962 | 55 | DdeI | 4 |
| CAPS | TG609 | IVT-1 | ATATGACTAGGAGGCAATGACTGA TTGCCTACTTATAACCCTGTGGA | 400 | 52 | AluI | 4 |
| CAPS | CT258 | IVT-1 | CAATGAATCATCTGTGGTGATT TGCATTCCTCTGTGGATGCT | 200 | 55 | HinfI | 4 |

TABLE 1-continued

Primer sequences and PCR reaction parameters for CAPS and SCAR markers

| Marker type | Name | Use | Primer (5'-3') $F_w$, $R_v$ | Size[a] (bp) | TA[b] (° C.) | Restriction enzyme | Chr[c] |
|---|---|---|---|---|---|---|---|
| SCAR | 114C15-S | ILs and IVT-1 | CTTAAATGCCGATGGAGGAG ATTTATGGGATGGATGATTTTC | 500, 450 c | 55 | | 4 |
| CAPS | At3g24010 | IVT-1 | ATGCAATCAGGATTGCTGATG CTGATCGAGCTGCTGAATATG | 1000 | 55 | TaqI | 9 |
| CAPS | T0156 | IVT-1 | GCGGTTGATTCACATCGTAA CCTGTAGCACCCAAAGGATG | 1100 | 55 | HpyCH4IV | 9 |
| CAPS | TG328 | IVT-1 | GAATGTCTAGTACCAGACTTAT AGTTCAATGTCCCTAGTTATAG | 350 | 55 | SpeI | 9 |
| CAPS | CT220 | IVT-1 | AAGCGAATTATCTGTCAAC GTTCCTGACCATTACAAAAGTAC | 200 | 55 | MseI | 9 |
| CAPS | T1065 | IVT-1 | GACGGTGAAGGGTACCAAG CAGGAGTGCATGGGTAGGT | 550 | 55 | SspI | 9 |
| CAPS | At5g06360 | IVT-1 | GGCTATGCATGAAGAGTCATC GGCACCTCCCATTTTCCAGC | 250 | 55 | ApoI | 9 |
| CAPS | CT229 | ILs | ATGGGCTGGGATCGTAGTAAA AAGCTTGCGATTCCCATAACAT | 336 | 55 | MwoI | 4 |
| CAPS | T0208 | ILs | AACGCCCCAGCCTGACTACA CTGGGGAGGTTTCGATTTCTG | 514 | 55 | HindIII | 4 |
| CAPS | TG483 | ILs | CACTCCCATGGCAGATAAAA AGTGAAGTAAAACAAAGCCAAAAT | 334 | 59 | HphI | 4 |
| CAPS | T0703 | ILs | ATTTTTACGGGCAAGCGACTG CGTTGATCCCTCTATAATGGTG | 456 | 55 | HpyCH4IV | 4 |
| CAPS | T1068 | ILs | CAAAGCAATGGGCAATGGT ACACAGCAGTTTCAGTAGGAC | 500 | 55 | HincII | 4 |
| CAPS | CT175 | ILs | CAGCTAAGCGTTGACAGTTGAGAA ATGGCCGCGGTTTGAGC | 750 | 55 | MseI | 4 |
| CAPS | TG182 | ILs | GCTCGGGCAACAGTGAAC GCTAAGCAAATGAAAAACCAGA | 335 | 55 | TaqI | 4 |
| CAPS | TG370 | ILs | ATGCTGCTGCCGGTTCCACT ATCGGGTCTCTAATTTCAGCAC | 352 | 55 | HpyCH4IV | 4 |
| CAPS | T0958 | ILs | GTGTCGAACCCTTGGCAACAAT AGTTCTTTCAGCTTTTGGGTTAA | 650 | 55 | RsaI | 4 |
| CAPS | T0891 | ILs | GACCGCTACCTCAACTTCT CACTCTAATACTCCACTCAACATA | 1200 | 55 | DraI | 4 |
| SCAR | TG339 | ILs | GAAACCTTACCCCTCTA CGCTGTTTCTTGCCATTT | 500, 436[e] | 46 | | 4 |
| SCAR | T0529 | ILs | TGGAGAGGAACAGGCTAAATC CACTCCGGCAACTGAAATGT | 1600, 1650[e] | 55 | | 4 |
| CAPS | T0635 | ILs and IVT-1 | CCAGAACCTCGACTCATCA TAGCCTCACAGTCTCAGTCAA | 300 | 55 | HincII | 4 |
| CAPS | TG60 | ILs | TTGGCTGAAGTGAAGAAAAGTA AAGGGCATTGTAATATCTGTCC | 1500 | 55 | HpyCH4IV | 5 |
| CAPS | CT138 | ILs | ACCAGCCCCGGAAGATTTTA GCGGTCAACTTCAGCAACTAT | 900 | 55 | RsaI | 5 |

[a] Size of undigested PCR product
[b] PCR annealing temperature
[c] Chromosome number
[d] Reference: Tanksley et al. (1992), Fulton et al. (2002)
[e] PCR product length on *S. habrochaites* and *S. lycopersicum* respectively

TABLE 2

Phenotypic means, peak LOD value, percentage explained variance and genetic action of 'logitPat' for pat-6, detected by Interval Mapping in population 5-1

| Trait | Genotype SL/SL | n | SL/SH | n | SH/SH | n | LOD | Explained variation |
|---|---|---|---|---|---|---|---|---|
| logitPat | −1.73 | (16) | −0.40 | (45) | −0.18 | (13) | 10.8 | 48.9% |
| AvPat[1] | 1.8% | | 28.3% | | 39.8% | | | |

[1]The logit numbers are transformed back into average pat ratio

TABLE 3

Observed parthenocarpy ratio for each parthenocarpy allele's combination of pat-6 and pat-7, in the $BC_5S_2$, in spring/summer and winter.

| | pat-7 (SL/SL) | | | | | pat-7 (SL/SH) | | | | | pat-7 (SH/SH) | | | |
|---|---|---|---|---|---|---|---|---|---|---|---|---|---|---|
| | spr/sum[1] | | winter | | | spr/sum | | winter | | | spr/sum | | winter | |
| pat-6 | Mean | SE[2] | Mean | SE | n[3] | Mean | SE | Mean | SE | n | Mean | SE | Mean | SE |
| SL/SL | 0.0 | 0.0 | 0.0 | 0.0 | (13) | 0.0 | 0.0 | 0.0 | 0.0 | (6) | 0.0 | 0.0 | 0.0 | 0.0 |
| SL/SH | 4.1 | 2.3 | 2.4 | 1.2 | (7) | 4.8 | 4.8 | 16.1 | 12.9 | (2) | 45.5 | 0.0 | 37.5 | 0.0 |
| SH/SH | 11.6 | 1.9 | 4.6 | 0.9 | (41) | 41.0 | 6.4 | 14.8 | 3.0 | (13) | 46.0 | 6.7 | 27.2 | 6.6 |

[1]spr/sum: Spring/summer
[2]SE: Standard Error
[3]n: Number of individuals per genotype category

TABLE 4

Significance of model [1] and estimates of the parameters

| | Spring/Summer | Winter |
|---|---|---|
| Probability of F | <0.001 | 0.001 |
| Coefficient Correlation | 64.8% | 57.9% |
| Constant ($\mu$) | −6.801 | −6.658 |
| Effect of SH allele of pat-6 ($\alpha_j$): | | |
| When pat-7 is SL/SL ($\alpha_1$) | 1.782 | 1.235 |
| When pat-7 is SL/SH ($\alpha_2$) | 3.101 | 2.439 |
| When pat-7 is SH/SH ($\alpha_3$) | 3.408 | 2.787 |

TABLE 5

Phenotypic means, peak LOD value, percentage explained variance and genetic action of 'stigma exertion', detected by Interval Mapping in $BC_5S_1$ population 5-1 and 5-2

| Trait | Genotype SL | n[1] | H | n | SH | n | LOD | Explained variation |
|---|---|---|---|---|---|---|---|---|
| Stigma exertion (mm) | −0.53 | (3) | 0.45 | (73) | 2.04 | (64) | 19.23 | 47.9% |

[1]n: Number of individuals per genotype category

TABLE 6

Observed parthenocarpy ratio for each parthenocarpy allele's combination of pat-8 and pat-9, in the $F_2$ population (n = 137).

| | pat-9 (SL/SL) | | | | pat-9 (SL/SH) | | | | pat-9 (SH/SH) | | | |
|---|---|---|---|---|---|---|---|---|---|---|---|---|
| pat-8 | Pred[1] | Obs[2] | SE | n | Pred | Obs | SE | n | Pred | Obs | SE | n |
| SL/SL | 0.0 | 0.3 | 0.2 | (14) | 0.0 | 0.8 | 0.4 | (24) | 0.0 | 0.4 | 0.4 | (4) |
| SL/SH | 0.0 | 0.2 | 0.2 | (14) | 0.1 | 12.3 | 2.7 | (40) | 87.5 | 65.2 | 6.0 | (12) |
| SH/SH | 0.0 | 0.0 | 0.0 | (8) | 7.1 | 29.2 | 4.4 | (17) | 97.1 | 76.6 | 12.8 | (4) |

[1]Predicted effect from regression model, transformed back into percentages
[2]Observed mean for each combination of alleles

REFERENCES

Beraldi D, Picarella M E, Soressi G P, Mazzucato A (2004) Fine mapping of the parthenocarpic fruit (pat) mutation in tomato. Theoretical and Applied Genetics 108: 209-216.

Bernacchi D, Tanksley S D (1997) An interspecific backcross of *Lycopersicon esculentum×L. hirsutum*: linkage analysis and a QTL study of sexual compatibility factors and floral traits. Genetics 147: 861-877.

Brouwer D J, St. Clair D A (2004) Fine mapping of three quantitative trait loci for late blight resistance in tomato using Near Isogenic Lines (NILs) and sub-NILs. Theoretical and Applied Genetics 108: 628-638.

Chetelat R T, Meglic V (2000) Molecular mapping of Chromosome segments introgressed from *Solanum lycopersicoides* into cultivated tomato (*L. esculentum*). Theoretical and Applied Genetics 100: 232-241.

Coaker G L, Francis D M (2004) Mapping, genetic effects, and epistatic interaction of two bacterial canker resistance QTLs from *Lycopersicon hirsutum*. Theoretical and Applied Genetics 108: 1047-1055.

Finkers R, van den Berg P, van Berloo R, ten Have A, van Heusden A W, van Kan J A L, Lindhout P (2007a) Three QTLs for Botrytis cinera resistance in tomato. Theoretical and Applied Genetics 114: 585-593.

Finkers R, van Heusden A W, Meijer-Dekens F, van Kan J A L, Maris P, Lindhout P (2007b) The Construction of a *Solanum habrochaites* LYC4 introgression line population and the identification of QTLs for resistance to Botrytis cinera. Theoretical and Applied Genetics 114: 1071-1080.

Fulton T M, van der Hoeven R, Eannetta N T, Tanksley S D (2002) Identification, analysis, and utilization of conserved ortholog set markers for comparative genomics in higher plants. The Plant Cell 14: 1457-1467.

Gorguet B, van Heusden A W, Lindhout P (2005) Parthenocarpic fruit development in tomato. Plant Biology 7: 131-139.

Gorguet B, Schipper D, van Heusden A W, Lindhout P (2006) High resolution fine mapping of ps-2, a mutated gene conferring functional male sterility in tomato due to non-dehiscent anthers. Theoretical and Applied Genetics. 113:1437-1448.

Monforte A J, Tanksley S D (2000) Development of a set of near isogenic and backcross recombinant inbred lines containing most of the *Lycopersicon hirsutum* genome in a *L. esculentum* genetic background: a tool for gene mapping and gene discovery. Genome 43: 803-813.

Mueller L A, Solow T H, Taylor N, Skwarecki B, Buels R, Binns J, Lin C, Wright, Ahrens R, Wang Y, Herbst E V, Keyder E R, Menda N, Zamir D, Tanksley S D (2005) The SOL Genomics Network. A Comparative Resource for Solanaceae Biology and Beyond. Plant Physiology 138: 1310-1317.

Paterson A H, De-Verna J W, Lanini B, Tanksley S D (1990) Fine mapping of quantitative trait loci using selected overlapping recombinant chromosomes, in an interspecific cross of tomato. Genetics 124: 735-742.

Picken A J F (1984) A review of pollination and fruit set in the tomato (*Lycopersicon esculentum* Mill.). Journal of Horticultural Science 59: 1-13.

Rick C M (1969) Controlled introgression of chromosomes from *Solanum pennellii* into *Lycopersicon esculentum*: segregation and recombination. Genetics 62: 753-768.

Steward C N, Via L E (1993) A rapid CTAB DNA isolation technique useful for RAPD fingerprinting and other PCR applications. BioTechniques 14: 748-750.

Tanksley S D, Ganal M W, Prince J P, de Vicente M C, Bonierbale M W, Broun P, Fulton T M, Giovannoni J J, Grandillo S, Martin G B, Messequer R, Miller J C, Miller L, Paterson A H, Pineda O, Roder M S, Wing R A, Wu W, Young N D (1992) High density molecular linkage maps of tomato and potato genomes. Genetics 132: 1141-1160.

Van Ooijen J W (1999) LOD significance thresholds for QTL analysis in experimental populations of diploid species. Heredity 83: 613-624.

Van Ooijen J W, Voorrips R E (2001) JoinMap® 3.0, Software for the calculation of genetic linkage maps. Plant Research International, Wageningen, the Netherlands.

Van Ooijen J W (2004) MapQTL® 5, Software for the mapping of quantitative trait loci in experimental populations. Kyazma B. V., Wageningen, The Netherlands.

Wang H, Qi M, Cutler A J (1993) A simple method of preparing plant samples for PCR. Nucleic Acids Research 21: 4153-4154.

Zijlstra S (1985) Parthenocarpie in tomaat; twee nieuwe lijnen uit soortkruising. Zaadbelangen 4: 92-94.

---

The invention claimed is:

1. A *Solanum lycopersicum* plant homozygous for a pat-6 parthenocarpy gene and homozygous for at least one of pat-8 and pat-9 parthenocarpy genes:
wherein the pat-6 gene is present on a DNA fragment from a segment of *S. habrochaites* chromosome 4 between markers TG182 and T0635;
wherein the pat-8 gene is present on a DNA fragment from a segment of *S. habrochaites* chromosome 4 between markers T0635 and TG287 or between markers T0958 and CT258, and
wherein the pat-9 gene is present on a DNA fragment from a segment of *S. habrochaites* chromosome 9 between markers TG1519 and At3g24010.

2. A *S. lycopersicum* plant according to claim 1, wherein the plant further comprises a pat-7 parthenocarpy gene, wherein the pat-7 gene is present on a DNA fragment from a segment of *S. habrochaites* chromosome 5 between markers TG441 and TG538 and is linked to the marker CD64.

3. A *S. lycopersicum* plant according to claim 2, wherein the plant is homozygous for the pat-7 gene.

4. A *S. lycopersicum* plant according to claim 2, wherein at least one of the pat-6, pat-7, pat-8, and pat-9 genes is a gene as present in the *S. lycopersicum* IVT line-1 or originates from *S. habrochaites* LYC4.

5. A *S. lycopersicum* plant according to claim 1, wherein the plant is homozygous for both the pat-8 and pat-9 genes.

6. A *S. lycopersicum* plant according to claim 5, wherein at least one of the pat-8 and pat-9 genes originates from *S. habrochaites* LYC4 or at least one of the pat-8 and pat-9 genes is a gene as present in the *S. lycopersicum* IVT line-1.

7. A *S. lycopersicum* plant according to claim 1, comprising *S. habrochaites* pat-8 and pat-9 parthenocarpy genes.

8. A *S. lycopersicum* plant homozygous for a *S. habrochaites* se functional sterility gene and homozygous for at least one of pat-8 and pat-9 parthenocarpy genes, wherein
the se gene is present on a DNA fragment from a segment of *S. habrochaites* chromosome 5 between markers TG538 and TG358 and is linked to the marker T318,
wherein the pat-8 gene is present on a DNA fragment from a segment of *S. habrochaites* chromosome 4 between markers T0635 and TG287 or between markers T0958 and CT258, and
wherein the pat-9 gene is present on a DNA fragment from a segment of *S. habrochaites* chromosome 9 between markers TG1519 and At3g24010.

9. A *S. lycopersicum* plant according to claim 8, wherein the *S. habrochaites* se gene is present on a DNA fragment that confers functional sterility as procured by stigma that exsert by at least 1.0 mm in a *S. lycopersicum* plant of the cultivar Moneymaker when the plant is homozygous for the DNA fragment.

10. A *S. lycopersicum* plant according to claim 8, wherein at least one of the pat-8 and pat-9 parthenocarpy genes or the *S. habrochaites* se gene is a gene as present in the *S. lycopersicum* IVT line-1 or the *S. habrochaites* se gene originates from *S. habrochaites* LYC4.

11. A *S. lycopersicum* plant according to claim 1, further comprising a *S. habrochaites* se functional sterility gene.

12. A *S. lycopersicum* plant according to claim 11, wherein the plant is homozygous for the se gene.

13. A *S. lycopersicum* plant according to any one of claim 1, wherein the plant is of a commercial tomato type selected from the group consisting of cherry, cocktail, mini plum, plum cocktail, plum, round, and beef.

14. A *S. lycopersicum* plant according to claim 13, wherein the plant is of a variety or cultivar selected from the group consisting of Claree, Conchita, Gisela, Favorita, Josefina, Lupita, Prolyco, Lycanto, Amoroso, WS4176, Aranca, Campari, Shiren, Panarea, Tyty, Santa, Santalina, Santella, WS4166, Dasher, Ginko, Balerina, Sunstream, Romana, Savantas, WS4178, WS4179, Reconquista, Recova, Yoga, Torro, Yaki, Durinta, Habana, Plaisance, Mecano, Tricia, Grandella, Bizarr, Brilliant, Axxion, Ingar, Espero, Cedrico, Emotion, Daniela, Aromata, Clotilde, Ever, Clarance, Letitia, Ikram, Boludo, Astona, Bravona, Benevita, Delikata, Admiro, Prego, Growdena, Birloque, Quest, Macarena, Carson, Rapsodi, Cunero, Kumato, Momotaro, Exota, Rosy, Yellow Gold, Orama, Carovita, and Vintage.

15. A *S. lycopersicum* plant according to claim 1, wherein the plant further comprises a parthenocarpic gene selected from the group consisting of pat, pat-1, pat-2, pat-3, pat-4, pat-5, ps-2, sha, and sds.

16. Seed that produces a *S. lycopersicum* plant as defined in claim 1.

17. Fruit from a *S. lycopersicum* plant as defined in claim 1.

18. A method for producing a *S. lycopersicum* plant that is homozygous for at least one of the pat-6, pat-7, pat-8, pat-9 and se genes, comprising
   (a) crossing a first *S. lycopersicum* plant with a second plant of the *Solanum Lycopersicum* complex that comprises at least one of the pat-6, pat-7, pat-8, pat-9 and se genes;
   (b) backcrossing the F1 generation and further generations for at least two generation with the first *S. lycopersicum* plant as a recurrent parent;
   (c) selfing the furthest backcrossed generation obtained in (b) for at least two generations; and,
   (d) selecting for a *S. lycopersicum* plant that is homozygous for at least one of the pat-6, pat-7, pat-8, pat-9 and se genes using at least one molecular marker in at least one of steps (b) and (c); wherein the molecular marker is diagnostic for the presence of
      the pat-6 gene present on a DNA fragment comprised within a segment of *S. habrochaites* chromosome 4 between markers TG182 and T0635,
      the pat-7 gene present on a DNA fragment comprised within a segment of *S. habrochaites* chromosome 5 between markers TG182 and T0635 and is linked to marker CD64,
      the pat-8 gene present on a DNA fragment comprised within a segment of *S. habrochaites* chromosome 4 between markers T0635 and TG287 or between markers T0958 and CT258,
      the pat-9 gene present on a DNA fragment comprised within a segment of *S. habrochaites* chromosome 9 between markers TG1519 and At3g24010, or
      the se gene present on a DNA fragment comprised within a segment of *S. habrochaites* chromosome 5 between markers TG538 and TG358 and is linked to the marker T318.

19. A method for producing a *S. lycopersicum* plant capable of carrying seedless tomatoes comprising:
   (a) crossing a first *S. lycopersicum* plant with a second plant of the *Solanum lycopersicum* complex that comprises at least one of the *S. habrochaites* pat-6, pat-7, pat-8 and pat-9 genes;
   (b) backcrossing the F1 generation and further generations for at least two generation with the first *S. lycopersicum* plant as a recurrent parent; and,
   (c) selfing the furthest backcrossed generation obtained in b) for at least two generations,
   (d) selecting for a *S. lycopersicum* plant comprising at least one of the pat-6, pat-7, pat-8 and pat-9 genes using at least one molecular marker in at least one of steps (b) and (c); wherein the molecular marker is diagnostic for the presence of
      the pat-6 gene present on a DNA fragment comprised within a segment of *S. habrochaites* chromosome 4 between markers TG182 and T0635,
      the pat-7 gene present on a DNA fragment comprised within a segment of *S. habrochaites* chromosome 5 between markers TG182 and T0635 and is linked to marker CD64,
      the pat-8 gene present on a DNA fragment comprised within a segment of *S. habrochaites* chromosome 4 between markers T0635 and TG287 or between markers T0958 and CT258, or
      the pat-9 gene present on a DNA fragment comprised within a segment of *S. habrochaites* chromosome 9 between markers TG1519 and At3g24010.

20. A method according to claim 18, wherein the molecular marker is selected from the group consisting of markers TG182, T0891, T0958, T0635, 114C15-S, TG609, SSR450, SSR94, CT258, TG441, CD64, TG538, At3g24010, T0156, SSR599, At5g06360, T1065, CT220, TG358 and T318.

21. The method according to claim 19, wherein the molecular marker is selected from the group consisting of markers TG182, T0891, T0958, T0635, 114C15-S, TG609, SSR450, SSR94, CT258, TG441, CD64, TG538, At3g24010, T0156, SSR599, At5g06360, T1065, CT220, TG358 and T318.

22. Seed that produces a *S. lycopersicum* plant as defined in claim 8.

23. Fruit from a *S. lycopersicum* plant as defined in claim 8.

24. A method for producing a seedless tomato, the method comprising cultivating a plant as defined in claim 8 under conditions conducive to the production of seedless tomatoes, and harvesting the tomatoes.

\* \* \* \* \*

SEQUENCE LISTING

```
<160> NUMBER OF SEQ ID NOS: 25

<210> SEQ ID NO 1
<211> LENGTH: 43
<212> TYPE: DNA
<213> ORGANISM: Artificial
<220> FEATURE:
<223> OTHER INFORMATION: Synthetic sequence

<400> SEQUENCE: 1
cttaaaggca cacttagatt cactgagaat tctcttgact gca                          43

<210> SEQ ID NO 2
<211> LENGTH: 47
<212> TYPE: DNA
<213> ORGANISM: Artificial
<220> FEATURE:
<223> OTHER INFORMATION: Synthetic sequence

<400> SEQUENCE: 2
```
atatgactag gaggcaatga ctgattgcct acttataacc ctgtgga                          47

<210> SEQ ID NO 3
<211> LENGTH: 42
<212> TYPE: DNA
<213> ORGANISM: Artificial
<220> FEATURE:
<223> OTHER INFORMATION: synthetic sequence

<400> SEQUENCE: 3
caatgaatca tctgtggtga tttgcattcc tctgtggatg ct                              42

<210> SEQ ID NO 4
<211> LENGTH: 43
<212> TYPE: DNA
<213> ORGANISM: Artificial
<220> FEATURE:
<223> OTHER INFORMATION: Synthetic sequence

<400> SEQUENCE: 4
cttaaatgcc gatggaggag atttatgggg atggatgatt ttc                             43

<210> SEQ ID NO 5
<211> LENGTH: 42
<212> TYPE: DNA
<213> ORGANISM: Artificial
<220> FEATURE:
<223> OTHER INFORMATION: Synthetic sequence

<400> SEQUENCE: 5
atgcaatcag gattgctgat gctgatcgag ctgctgaata tg                              42

<210> SEQ ID NO 6
<211> LENGTH: 40
<212> TYPE: DNA
<213> ORGANISM: Artificial
<220> FEATURE:
<223> OTHER INFORMATION: Synthetic sequence

<400> SEQUENCE: 6
gcggttgatt cacatcgtaa cctgtagcac ccaaaggatg                                 40

<210> SEQ ID NO 7
<211> LENGTH: 44
<212> TYPE: DNA
<213> ORGANISM: Artificial
<220> FEATURE:
<223> OTHER INFORMATION: Synthetic sequence

<400> SEQUENCE: 7
gaatgtctag taccagactt atagttcaat gtccctagtt atag                            44

<210> SEQ ID NO 8
<211> LENGTH: 42
<212> TYPE: DNA
<213> ORGANISM: Artificial
<220> FEATURE:
<223> OTHER INFORMATION: Synthetic sequence

<400> SEQUENCE: 8
aagcgaatta tctgtcaacg ttcctgacca ttacaaaagt ac                              42

<210> SEQ ID NO 9
<211> LENGTH: 38
<212> TYPE: DNA

<213> ORGANISM: Artificial
<220> FEATURE:
<223> OTHER INFORMATION: Synthetic sequence

<400> SEQUENCE: 9
gacggtgaag ggtaccaagc aggagtgcat gggtaggt                                    38

<210> SEQ ID NO 10
<211> LENGTH: 41
<212> TYPE: DNA
<213> ORGANISM: Artificial
<220> FEATURE:
<223> OTHER INFORMATION: Synthetic sequence

<400> SEQUENCE: 10
ggctatgcat gaagagtcat cggcacctcc cattttccag c                                41

<210> SEQ ID NO 11
<211> LENGTH: 43
<212> TYPE: DNA
<213> ORGANISM: Artificial
<220> FEATURE:
<223> OTHER INFORMATION: Synthetic sequence

<400> SEQUENCE: 11
atgggctggg atcgtagtaa aaagcttgcg attcccataa cat                              43

<210> SEQ ID NO 12
<211> LENGTH: 41
<212> TYPE: DNA
<213> ORGANISM: Artificial
<220> FEATURE:
<223> OTHER INFORMATION: Synthetic sequence

<400> SEQUENCE: 12
aacgccccag cctgactaca ctggggaggt ttcgatttct g                                41

<210> SEQ ID NO 13
<211> LENGTH: 44
<212> TYPE: DNA
<213> ORGANISM: Artificial
<220> FEATURE:
<223> OTHER INFORMATION: Synthetic sequence

<400> SEQUENCE: 13
cactcccatg gcagataaaa agtgaagtaa aacaaagcca aaat                             44

<210> SEQ ID NO 14
<211> LENGTH: 43
<212> TYPE: DNA
<213> ORGANISM: Artificial
<220> FEATURE:
<223> OTHER INFORMATION: Synthetic sequence

<400> SEQUENCE: 14
atttttacgg gcaagcgact gcgttgatcc ctctataatg gtg                              43

<210> SEQ ID NO 15
<211> LENGTH: 40
<212> TYPE: DNA
<213> ORGANISM: Artificial
<220> FEATURE:
<223> OTHER INFORMATION: Synthetic sequence

<400> SEQUENCE: 15
caaagcaatg ggcaatggta cacagcagtt tcagtaggac                                  40

<210> SEQ ID NO 16
<211> LENGTH: 41
<212> TYPE: DNA
<213> ORGANISM: Artificial
<220> FEATURE:
<223> OTHER INFORMATION: Synthetic sequence

<400> SEQUENCE: 16
cagctaagcg ttgacagttg agaaatggcc gcggtttgag c                          41

<210> SEQ ID NO 17
<211> LENGTH: 40
<212> TYPE: DNA
<213> ORGANISM: Artificial
<220> FEATURE:
<223> OTHER INFORMATION: Synthetic sequence

<400> SEQUENCE: 17
gctcgggcaa cagtgaacgc taagcaaatg aaaaaccaga                            40

<210> SEQ ID NO 18
<211> LENGTH: 42
<212> TYPE: DNA
<213> ORGANISM: Artificial
<220> FEATURE:
<223> OTHER INFORMATION: Synthetic sequence

<400> SEQUENCE: 18
atgctgctgc cggttccact atcgggtctc taatttcagc ac                         42

<210> SEQ ID NO 19
<211> LENGTH: 45
<212> TYPE: DNA
<213> ORGANISM: Artificial
<220> FEATURE:
<223> OTHER INFORMATION: Synthetic sequence

<400> SEQUENCE: 19
gtgtcgaacc cttggcaaca atagttcttt cagcttttgg gttaa                      45

<210> SEQ ID NO 20
<211> LENGTH: 43
<212> TYPE: DNA
<213> ORGANISM: Artificial
<220> FEATURE:
<223> OTHER INFORMATION: Synthetic sequence

<400> SEQUENCE: 20
gaccgctacc tcaacttctc actctaatac tccactcaac ata                        43

<210> SEQ ID NO 21
<211> LENGTH: 35
<212> TYPE: DNA
<213> ORGANISM: Artificial
<220> FEATURE:
<223> OTHER INFORMATION: Synthetic sequence

<400> SEQUENCE: 21
gaaaccttac ccctctacgc tgtttcttgc cattt                                 35

<210> SEQ ID NO 22
<211> LENGTH: 41
<212> TYPE: DNA
<213> ORGANISM: Artificial
<220> FEATURE:

```
<223> OTHER INFORMATION: Synthetic sequence

<400> SEQUENCE: 22
tggagaggaa caggctaaat ccactccggc aactgaaatg t                          41

<210> SEQ ID NO 23
<211> LENGTH: 40
<212> TYPE: DNA
<213> ORGANISM: Artificial
<220> FEATURE:
<223> OTHER INFORMATION: Synthetic sequence

<400> SEQUENCE: 23
ccagaacctc gactcatcat agcctcacag tctcagtcaa                            40

<210> SEQ ID NO 24
<211> LENGTH: 44
<212> TYPE: DNA
<213> ORGANISM: Artificial
<220> FEATURE:
<223> OTHER INFORMATION: Synthetic sequence

<400> SEQUENCE: 24
ttggctgaag tgaagaaaag taaagggcat tgtaatatct gtcc                       44

<210> SEQ ID NO 25
<211> LENGTH: 41
<212> TYPE: DNA
<213> ORGANISM: Artificial
<220> FEATURE:
<223> OTHER INFORMATION: Synthetic sequence

<400> SEQUENCE: 25
accagccccg gaagatttta gcggtcaact tcagcaacta t                          41
```